(12) United States Patent
McEachern et al.

(10) Patent No.: US 9,522,883 B2
(45) Date of Patent: Dec. 20, 2016

(54) GLYCOSIDASE INHIBITORS AND USES THEREOF

(71) Applicants: Alectos Therapeutics Inc., Burnaby (CA); Merck Sharp & Dohme Corp., Rahway, NJ (US)

(72) Inventors: Ernest J. McEachern, Vancouver (CA); David J. Vocadlo, Burnaby (CA); Yuanxi Zhou, Burnaby (CA); Harold G. Selnick, West Point, PA (US)

(73) Assignees: Alectos Therapeutics Inc., Burnaby (CA); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/424,602

(22) PCT Filed: Aug. 29, 2013

(86) PCT No.: PCT/CA2013/050671
§ 371 (c)(1),
(2) Date: Feb. 27, 2015

(87) PCT Pub. No.: WO2014/032187
PCT Pub. Date: Mar. 6, 2014

(65) Prior Publication Data
US 2015/0218097 A1 Aug. 6, 2015

Related U.S. Application Data

(60) Provisional application No. 61/696,003, filed on Aug. 31, 2012.

(51) Int. Cl.
| | |
|---|---|
| *C07D 211/56* | (2006.01) |
| *A61K 31/445* | (2006.01) |
| *A61K 31/4523* | (2006.01) |
| *C07D 401/06* | (2006.01) |
| *C07D 417/06* | (2006.01) |

(52) U.S. Cl.
CPC ........... *C07D 211/56* (2013.01); *A61K 31/445* (2013.01); *A61K 31/4523* (2013.01); *C07D 401/06* (2013.01); *C07D 417/06* (2013.01)

(58) Field of Classification Search
CPC ...... C07D 211/56; C07D 41/06; C07D 417/06
USPC ........................................................ 546/240
See application file for complete search history.

(56) References Cited

U.S. PATENT DOCUMENTS

| | | | | |
|---|---|---|---|---|
| 4,871,747 A * | 10/1989 | Kinast | ................... | C07D 211/46 514/315 |
| 5,276,120 A * | 1/1994 | Wong | ..................... | C07C 247/04 546/184 |
| 6,291,657 B1 * | 9/2001 | Platt | ...................... | C07D 211/46 536/17.2 |
| 2001/0027195 A1 * | 10/2001 | Nugiel | ................. | C07D 231/54 514/232.8 |

FOREIGN PATENT DOCUMENTS

| | | | |
|---|---|---|---|
| AT | 507745 | * | 7/2010 |
| EP | 304731 | * | 3/1989 |
| WO | 2006100586 | * | 9/2006 |
| WO | 2010049678 | * | 5/2010 |
| WO | WO-2012/127506 A1 | | 9/2012 |
| WO | WO2011098 | * | 1/2013 |

OTHER PUBLICATIONS

Furneaus et al. "2—acetamido. . . . . " Abstract Tetrahedron 49(41)9605-12 (1993).*
Kaijimoto et al. "Enayme catalyzed . . . . " J. Am. Chem. soc. 113, 6187-96 (1991).*
Rejman et al. "The synthesis . . . . " Eur. J. Org. Chem. 11, 2172-87 (20110.*
Burger et al. "N-pyridinyl . . . . " CA151:358734 (2009).*
Le Huerou et al. "Preparation . . . . " CA151:550551 (2009).*
Ninkovic et al. "Preparation of hetero . . . . " CA152 :262750 (2010).*
Shirai et al. "Preparation of pyrani . . . . " CA147:277688 (2007).*
Glawar et al. "Scalable synthesis . . . . " Chem. Eur. J. 18:9341-59 (2012).*
Greene "Protective groups . . . . " p. 218-220, 224, 251 (1982).*
Glawar et al. "Scalable synthesis " Chem. Eur. J. 18 p. 9341-9359 (2012).*
de la Fuente et al., "Stereoselective synthesis of 2-acetamido-1,2-dideoxyallonojirimycin (DAJNAc), a new potent hexosaminidase inhibitor," Org Lett. 15(14):3638-41 (2013).
International Preliminary Report for International Application No. PCT/CA2013/050671, issued Mar. 3, 2015 (10 pages).
Written Opinion and International Search Report for International Application No. PCT/CA2013/050671, mailed on Nov. 7, 2013 (19 pages).

* cited by examiner

*Primary Examiner* — Celia Chang
(74) *Attorney, Agent, or Firm* — Clark & Elbing LLP

(57) ABSTRACT

The invention provides compounds of Formula (I) for inhibiting gh cosidases, prodrugs of the compounds, and pharmaceutical compositions comprising the compounds or prodrugs of the compounds. The invention also provides method of treating diseases and disorders related to deficiency or over-expression of O-gh coprotein 2-acetamido-2-deoxy-β-D-glucopyranosidase (O-GlcNAcase), accumulation or deficiency of 2-acetamido-2-deoxy-β-D-glucopyranoside (O-GlcNAc).

(I)

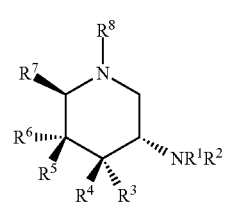

9 Claims, No Drawings

GLYCOSIDASE INHIBITORS AND USES THEREOF

FIELD OF THE INVENTION

This application relates to compounds which inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as glycoprotein 2-acetamido-2-deoxy-β-D-glucopyranosidase (O-GlcNAcase)[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the brain.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27-29] The precise causes of this hyperphosphorylation of tau remain elusive. Accordingly, considerable effort has been dedicated toward: a) elucidating the molecular physiological basis of tau hyperphosphorylation;[30] and b) identifying strategies that could limit tau hyperphosphorylation in the hope that these might halt, or even reverse, the progression of Alzheimer's disease[31-34] Thus far, several lines of evidence suggest that up-regulation of a number of kinases may be involved in hyperphosphorylation of tau,[21,35,36] although it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[54] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[55,56] and binding partners[42,57] through its tetratricopeptide repeat In particular, it has emerged that phosphate levels of tau are regulated by the levels of O-GlcNAc on tau. The presence of O-GlcNAc on tau has stimulated studies that correlate O-GlcNAc levels with tau phosphorylation levels. The interest in this field stems from the observation that O-GlcNAc modification has been found to occur on many proteins at amino acid residues that are also known to be phosphorylated.[37-39] Consistent with this observation, it has been found that increases in phosphorylation levels result in decreased O-GlcNAc levels and conversely, increased O-GlcNAc levels correlate with decreased phosphorylation levels.[40] This reciprocal relationship between O-GlcNAc and phosphorylation has been termed the "Yin-Yang hypothesis"[41] and has gained strong biochemical support by the discovery that the enzyme OGT[4] forms a functional complex with phosphatases that act to remove phosphate groups from proteins.[42] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,43] Hyperphosphorylated tau in human AD brains has markedly lower levels of O-GlcNAc than are found in healthy human brains.[21] It has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[44] Within the brains of AD patients marked decreases in glucose utilization occur and are thought to be a potential cause of neurodegeneration.[45] The basis for this decreased glucose supply in AD brain[46-48] is thought to stem from any of decreased glucose transport,[49,50] impaired insulin signaling,[51,52] and decreased blood flow.[53]

In light of this impaired glucose metabolism, it is worth very recently, an alternative basis for this hyperphosphorylation has been advanced.[21]

(TPR) domains.[58,59] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites[10,38,39,60] including tau and neurofilaments.[61] Additionally, OGT shows unusual kinetic behaviour making it exquisitely sensitive to intracellular UDP-GlcNAc substrate concentrations and therefore glucose supply.[42]

Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[45] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[62] comes from recent studies showing that when transgenic mice harbouring human tau are treated with kinase inhibitors, they do not develop typical motor defects[34] and, in another case,[33] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[63]

Small-molecule O-GlcNAcase inhibitors, to limit tau hyperphosphorylation, have been considered for treatment of AD and related tauopathies.[64] Specifically, the O-GlcNAcase inhibitor thiamet-G has been implicated in the reduction of tau phosphorylation in cultured PC-12 cells at pathologically relevant sites.[64] Moreover, oral administration of thiamet-G to healthy Sprague-Dawley rats has been implicated in reduced phosphorylation of tau at Thr231, Ser396 and Ser422 in both rat cortex and hippocampus.[64]

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion,[65-71] trauma hemorrhage,[72-74] hypervolemic shock,[75] and calcium paradox.[65,76] Moreover, strong evidence indicates that these cardioprotective effects are mediated by elevated levels of protein O-GlcNAc modification.[65,66,68,71,73,76-79] There is also evidence that the O-GlcNAc modification plays a role in a variety of neurodegenerative diseases, including Parkinson's disease and Huntington's disease.[80]

Humans have three genes encoding enzymes that cleave terminal β-N-acetylglucosamine residues from glycoconjugates. The first of these encodes O-GlcNAcase. O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[81,82] O-GlcNAcase acts to hydrolyse O-GlcNAc off of serine and threonine residues of post-translationally modified proteins.[1,6,7,83,84] Consistent with the presence of O-GlcNAc on many intracellular proteins, the enzyme O-GlcNAcase appears to have a role in the etiology of several diseases including type II diabetes[14,85] AD[16,21,86] and cancer.[22,87] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[88] These enzymatic deficiencies cause an accumulation of glycolipids and glycoconjugates in the lysosomes resulting in neurological impairment and deformation. The deleterious effects of accumulation of gangliosides at the organismal level are still being uncovered.[89]

As a result of the biological importance of these β-N-acetyl-glucosaminidases, small molecule inhibitors of glycosidases[90-93] have received a great deal of attention,[94] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, many compounds that act to block O-GlcNAcase function are non-specific and act potently to inhibit the lysosomal β-hexosaminidases.

A few of the better characterized inhibitors of β-N-acetylglucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenylcarbamate (PUGNAc).[14,95-98]

STZ has long been used as a diabetogenic compound because it has a particularly detrimental effect on β-islet cells.[99] STZ exerts its cytotoxic effects through both the alkylation of cellular DNA[99,100] as well as the generation of radical species including nitric oxide.[101] The resulting DNA strand breakage promotes the activation of poly(ADP-ribose) polymerase (PARP)[102] with the net effect of depleting cellular NAD+ levels and, ultimately, leading to cell death.[103,104] Other investigators have proposed instead that STZ toxicity is a consequence of the irreversible inhibition of O-GlcNAcase, which is highly expressed within β-islet cells.[95,105] This hypothesis has, however, been brought into question by two independent research groups.[106,107] Because cellular O-GlcNAc levels on proteins increase in response to many forms of cellular stress[108] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[109] and although it has been proposed by others that STZ acts to irreversibly inhibit O-GlcNAcase,[110] there has been no clear demonstration of this mode of action. More recently, it has been shown that STZ does not irreversibly inhibit O-GlcNAcase.[111]

NAG-thiazoline has been found to be a potent inhibitor of family 20 hexosaminidases,[93,112] and more recently, the family 84 O-GlcNAcases.[111] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,113] and the family 20 human β-hexosaminidases.[114] This molecule, developed by Vasella and coworkers, was found to be a potent competitive inhibitor of the β-N-acetyl-glucosaminidases from Canavalia ensiformis, Mucor rouxii, and the β-hexosaminidase from bovine kidney.[91] It has been demonstrated that administration of PUGNAc in a rat model of trauma hemorrhage decreases circulating levels of the pro-inflammatory cytokines TNF-α and IL-6.[115] It has also been shown that administration of PUGNAc in a cell-based model of lymphocyte activation decreases production of the cytokine IL-2.[116] Subsequent studies have indicated that PUGNAc can be used in an animal model to reduce myocardial infarct size after left coronary artery occlusions.[117] Of particular significance is the fact that elevation of O-GlcNAc levels by administration of PUGNAc, an inhibitor of O-GlcNAcase, in a rat model of trauma hemorrhage improves cardiac function.[115,118] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[119]

More recently, it has been suggested that the selective O-GlcNAcase inhibitor NButGT exhibits protective activity in cell-based models of ischemia/reperfusion and cellular stresses, including oxidative stress.[120] This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar. 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; PCT/CA2009/001302, filed 16 Sep. 2009, published under WO 2010/037207 on 8 Apr. 2010; PCT/CA2011/000548, filed 10 May 2011, published under No. WO 2011/140640 on 17 Nov. 2011; PCT/CA/2011/001241, filed 8 Nov. 2011, published under WO 2012/061927 on 18 May 2012; PCT/US2011/059668, filed 8 Nov. 2011, published under WO 2012/064680 on 18 May 2012; and PCT/CA2011/001397, filed 21 Dec. 2011, published under WO 2012/083435 on 28 Jun. 2012, describe selective inhibitors of O-GlcNAcase.

SUMMARY OF THE INVENTION

The invention provides, in part, compounds for inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, and/or accumulation or deficiency of O-GlcNAc.

In one aspect, the invention provides a compound of Formula (I) or a pharmaceutically acceptable salt thereof:

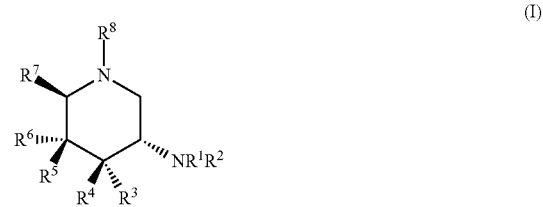

(I)

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (I) in which at least one of $R^3$, $R^4$, $R^5$, or $R^6$ may be OH; or $R^7$ may be $CH_2OH$.

In alternative embodiments, the invention provides a compound of Formula (I) in which at least one of $R^3$, $R^4$, $R^5$, or $R^6$ may be F; or $R^7$ may be $CH_2F$ or $CHF_2$.

In alternative embodiments, the invention provides a compound of Formula (I) in which $R^3$ and $R^4$ may be H; or $R^5$ and $R^6$ may be H; or $R^7$ may be $CH_3$.

In alternative embodiments, the invention provides a compound of Formula (I) in which at least one of $R^3$, $R^4$, $R^5$, $R^6$, or $R^7$ may be other than H.

In alternative embodiments, the invention provides a compound of Formula (I) in which at least one of $R^3$ or $R^4$ may be other than H.

In alternative embodiments, the invention provides a compound of Formula (I) in which at least one of $R^5$ or $R^6$ may be other than H.

In alternative embodiments, the invention provides a compound of Formula (I) in which $R^7$ may be H.

In alternative embodiments, the invention provides a compound of Formula (I) in which $R^7$ may be other than H.

In alternative embodiments, the invention provides a compound of Formula (I) in which $R^7$ may be other than $CH_3$.

In alternative embodiments, the invention provides a compound of Formula (I) in which $R^8$ may be other than H.

In alternative embodiments, the invention provides a compound of Formula (Ia) or a pharmaceutically acceptable salt thereof:

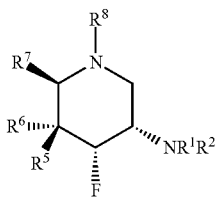

(Ia)

where $R^1$ may be H or $C_{1-6}$ alkyl; $R^2$ may be $C_{1-6}$ acyl; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ib) or a pharmaceutically acceptable salt thereof:

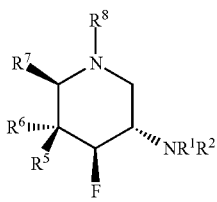

(Ib)

where $R^1$ may be H or $C_{1-6}$ alkyl; $R^2$ may be $C_{1-6}$ acyl; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ic) or a pharmaceutically acceptable salt thereof:

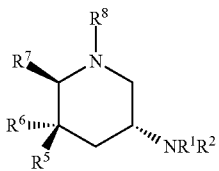

(Ic)

where $R^1$ may be H or $C_{1-6}$ alkyl; $R^2$ may be $C_{1-6}$ acyl; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ hetero arylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Id) or a pharmaceutically acceptable salt thereof:

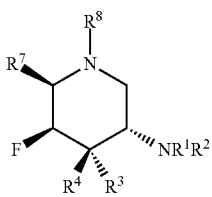

(Id)

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl.

In alternative embodiments, the invention provides a compound of Formula (Ie) or a pharmaceutically acceptable salt thereof:

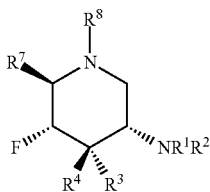

(Ie)

where R$^1$ may be H or C$_{1-6}$ alkyl; R$^2$ may be C$_{1-6}$ acyl; R$^3$ may be H and R$^4$ may be OH, or R$^3$ may be H and R$^4$ may be H, or R$^3$ may be H and R$^4$ may be F, or R$^3$ may be F and R$^4$ may be H, or R$^3$ may be F and R$^4$ may be F, or R$^3$ may be OH and R$^4$ may be H; R$^7$ may be selected from the group consisting of: H, CH$_3$, CH$_2$F, CHF$_2$, and CH$_2$OH; and R$^8$ may be selected from the group consisting of: H, C$_{1-10}$ alkyl, C$_{2-10}$ alkenyl, C$_{2-10}$ alkynyl, C$_{1-10}$ acyl, C$_{8-20}$ arylalkylacyl, C$_{3-20}$ heteroarylalkylacyl, C$_{7-20}$ arylalkyl, C$_{8-20}$ arylalkenyl, C$_{8-20}$ arylalkynyl, C$_{2-20}$ heteroarylalkyl, C$_{3-20}$ heteroarylalkenyl, and C$_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl.

In alternative embodiments, the invention provides a compound of Formula (If) or a pharmaceutically acceptable salt thereof:

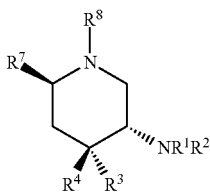

(If)

where R$^1$ may be H or C$_{1-6}$ alkyl; R$^2$ may be C$_{1-6}$ acyl; R$^3$ may be H and R$^4$ may be OH, or R$^3$ may be H and R$^4$ may be H, or R$^3$ may be H and R$^4$ may be F, or R$^3$ may be F and R$^4$ may be H, or R$^3$ may be F and R$^4$ may be F, or R$^3$ may be OH and R$^4$ may be H; R$^7$ may be selected from the group consisting of: H, CH$_3$, CH$_2$F, CHF$_2$, and CH$_2$OH; and R$^8$ may be selected from the group consisting of: H, C$_{1-10}$ alkyl, C$_{2-10}$ alkenyl, C$_{2-10}$ alkynyl, C$_{1-10}$ acyl, C$_{8-20}$ arylalkylacyl, C$_{3-20}$ heteroarylalkylacyl, C$_{7-20}$ arylalkyl, C$_{8-20}$ arylalkenyl, C$_{8-20}$ arylalkynyl, C$_{2-20}$ heteroarylalkyl, C$_{3-20}$ heteroarylalkenyl, and C$_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl.

In alternative embodiments, the invention provides a compound of Formula (Ig) or a pharmaceutically acceptable salt thereof:

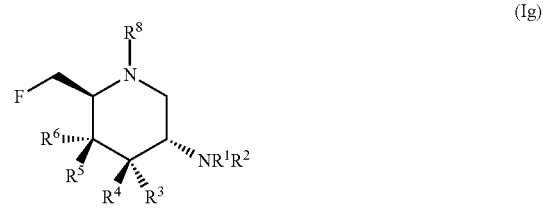

(Ig)

where R$^1$ may be H or C$_{1-6}$ alkyl; R$^2$ may be C$_{1-6}$ acyl; R$^3$ may be H and R$^4$ may be OH, or R$^3$ may be H and R$^4$ may be H, or R$^3$ may be H and R$^4$ may be F, or R$^3$ may be F and R$^4$ may be H, or R$^3$ may be F and R$^4$ may be F, or R$^3$ may be OH and R$^4$ may be H; R$^5$ may be H and R$^6$ may be OH, or R$^5$ may be H and R$^6$ may be H, or R$^5$ may be H and R$^6$ may be F, or R$^5$ may be F and R$^6$ may be H, or R$^5$ may be F and R$^6$ may be F, or R$^5$ may be OH and R$^6$ may be H; and R$^8$ may be selected from the group consisting of: H, C$_{1-10}$ alkyl, C$_{2-10}$ alkenyl, C$_{2-10}$ alkynyl, C$_{1-10}$ acyl, C$_{8-20}$ arylalkylacyl, C$_{3-20}$ heteroarylalkylacyl, C$_{7-20}$ arylalkyl, C$_{8-20}$ arylalkenyl, C$_{8-20}$ arylalkynyl, C$_{2-20}$ heteroarylalkyl, C$_{3-20}$ heteroarylalkenyl, and C$_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl.

In alternative embodiments, the invention provides a compound of Formula (Ih) or a pharmaceutically acceptable salt thereof:

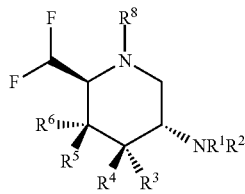

(Ih)

where R$^1$ may be H or C$_{1-6}$ alkyl; R$^2$ may be C$_{1-6}$ acyl; R$^3$ may be H and R$^4$ may be OH, or R$^3$ may be H and R$^4$ may be H, or R$^3$ may be H and R$^4$ may be F, or R$^3$ may be F and R$^4$ may be H, or R$^3$ may be F and R$^4$ may be F, or R$^3$ may be OH and R$^4$ may be H; R$^5$ may be H and R$^6$ may be OH, or R$^5$ may be H and R$^6$ may be H, or R$^5$ may be H and R$^6$ may be F, or R$^5$ may be F and R$^6$ may be H, or R$^5$ may be F and R$^6$ may be F, or R$^5$ may be OH and R$^6$ may be H; and R$^8$ may be selected from the group consisting of: H, C$_{1-10}$ alkyl, C$_{2-10}$ alkenyl, C$_{2-10}$ alkynyl, C$_{1-10}$ acyl, C$_{8-20}$ arylalkylacyl, C$_{3-20}$ heteroarylalkylacyl, C$_{7-20}$ arylalkyl, C$_{8-20}$ arylalkenyl, C$_{8-20}$ arylalkynyl, C$_{2-20}$ heteroarylalkyl, C$_{3-20}$ heteroarylalkenyl, and C$_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl.

In alternative embodiments, the invention provides a compound of Formula (Ii) or a pharmaceutically acceptable salt thereof:

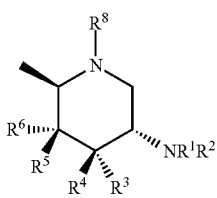
(Ii)

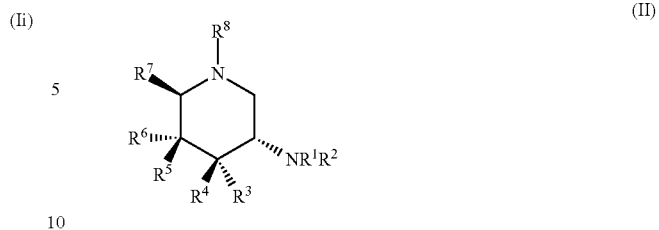
(II)

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (Ij) or a pharmaceutically acceptable salt thereof:

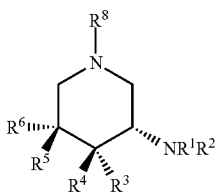
(Ij)

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In alternative embodiments, the invention provides a compound of Formula (II) or a pharmaceutically acceptable salt thereof:

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl; with the proviso that $R^8$ excludes benzyl, $CH(phenyl)_2$, and $C(O)CH_3$.

In alternative embodiments, the compound may be a prodrug; the compound may selectively inhibit an O-glycoprotein 2-acetamido-2-deoxy-β-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative embodiments, a compound according to Formula (I), Formula (Ia), Formula (Ib), Formula (Ic), Formula (Id), Formula (Ie), Formula (If), Formula (Ig), Formula (Ih), Formula (Ii), or Formula (Ij) may have enhanced permeability.

In alternative embodiments, a compound according to Formula (I) may have enhanced selectivity.

In alternative embodiments, a compound according to Formula (Ia), Formula (Ib), Formula (Id), Formula (Ie), Formula (Ig), or Formula (Ih) may have enhanced permeability.

In alternative embodiments, a compound according to Formula (Ic), Formula (If), Formula (Ii), or Formula (Ij) may have enhanced permeability.

In alternative aspects, the invention provides a pharmaceutical composition including a compound according to the invention, in combination with a pharmaceutically acceptable carrier.

In alternative aspects, the invention provides methods of selectively inhibiting an O-GlcNAcase, or of inhibiting an O-GlcNAcase in a subject in need thereof, or of increasing the level of O-GlcNAc, or of treating a neurodegenerative disease, a tauopathy, cancer or stress, in a subject in need thereof, by administering to the subject an effective amount of a compound of Formula (I) or a pharmaceutically acceptable salt thereof:

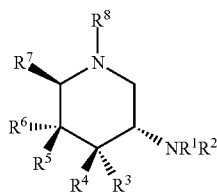 (I)

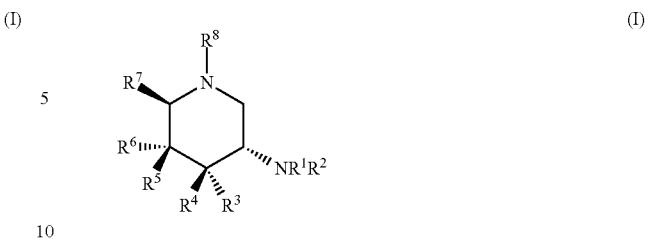 (I)

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. The condition may be Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, Parkinson's disease, Schizophrenia, Mild Cognitive Impairment (MCI), Neuropathy (including peripheral neuropathy, autonomic neuropathy, neuritis, and diabetic neuropathy), or Glaucoma. The stress may be a cardiac disorder, e.g., ischemia; hemorrhage; hypovolemic shock; myocardial infarction; an interventional cardiology procedure; cardiac bypass surgery; fibrinolytic therapy; angioplasty; or stent placement.

In alternative aspects, the invention provides a method of treating an O-GlcNAcase-mediated condition that excludes a neurodegenerative disease, a tauopathy, cancer or stress, in a subject in need thereof, by administering to the subject an effective amount of a compound of Formula (I) or a pharmaceutically acceptable salt thereof:

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl. In some embodiments, the condition may be inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, and eosiniphilic fasciitis; graft rejection, in particular but not limited to solid organ transplants, such as heart, lung, liver, kidney, and pancreas transplants (e.g. kidney and lung allografts); epilepsy; pain; fibromyalgia; stroke, e.g., neuroprotection following a stroke.

In alternative embodiments, the administering may increase the level of O-GlcNAc in the subject. The subject may be a human.

In alternative aspects, the invention provides use of a compound of an effective amount of a compound of Formula (I) or a pharmaceutically acceptable salt thereof:

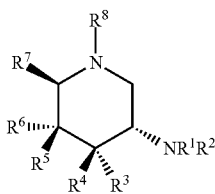

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl, in the preparation of a medicament. The medicament may be for selectively inhibiting an O-GlcNAcase, for increasing the level of O-GlcNAc, for treating a condition modulated by an O-GlcNAcase, for treating a neurodegenerative disease, a tauopathy, a cancer, or stress.

In alternative aspects, the invention provides a method for screening for a selective inhibitor of an O-GlcNAcase, by a) contacting a first sample with a test compound; b) contacting a second sample with a compound of Formula (I)

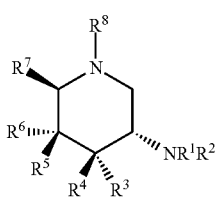

where $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl; c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formula (I).

This summary of the invention does not necessarily describe all features of the invention.

DETAILED DESCRIPTION

The invention provides, in part, novel compounds that are capable of inhibiting an O-glycoprotein 2-acetamido-2-deoxy-β-D-glucopyranosidase (O-GlcNAcase). In some embodiments, the O-GlcNAcase may be a mammalian O-GlcNAcase, such as a rat, mouse or human O-GlcNAcase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability ($P_{eff}$) or apparent permeability ($P_{app}$) are reviewed for example by Volpe in *The AAPS Journal*, 2010, 12(4), 670-678. In some embodiments, one or more of the compounds according to the invention may show enhanced permeability when tested in one or more of these assays for determining $P_{eff}$ or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, (3aR,5R,6S,7R,7aR)-5-(hydroxymethyl)-2-propyl-5,6,7,7a-tetrahydro-3aH-pyrano[3,2-d]thiazole-6,7-diol, or (3aR,5R,6S,7R,7aR)-2-(ethylamino)-5-(hydroxymethyl)-5,6,7,7a-tetrahydro-3aH-pyrano[3,2-d]thiazole-6,7-diol, or (3aR,5R,6S,7R,7aR)-2-(dimethylamino)-5-(hydroxymethyl)-5,6,7,7a-tetrahydro-3aH-pyrano[3,2-d]thiazole-6,7-diol. In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2 \times 10^{-6}$ cm/s in the assay described below for determination of $P_{app}$ in LLC-PK1 cells. In alternative embodiments, "enhanced permeability" means a $P_{app}$ value in the range $2 \times 10^{-6}$ CM/S to $35 \times 10^{-6}$ cm/s in the assay described below for determination of $P_{app}$ in LLC-PK1 cells.

In some embodiments, a compound according to the invention may exhibit superior selectivity in inhibiting an O-GlcNAcase. In some embodiments, one or more of the compounds according to the invention may be more selective for an O-GlcNAcase over a β-hexosaminidase. In some embodiments, one or more of the compounds may selectively inhibit the activity of a mammalian O-GlcNAcase over a mammalian β-hexosaminidase. In some embodiments, a selective inhibitor of an O-GlcNAcase may not substantially inhibit a β-hexosaminidase. In some embodiments, the β-hexosaminidase may be a mammalian β-hexosaminidase, such as a rat, mouse or human β-hexosaminidase. A compound that "selectively" inhibits an O-GlcNAcase is a compound that may inhibit the activity or biological function of an O-GlcNAcase, but may not substantially inhibit the activity or biological function of a β-hexosaminidase. For example, in some embodiments, a selective inhibitor of an O-GlcNAcase may selectively inhibit the cleavage of 2-acetamido-2-deoxy-β-D-glucopyranoside (O-GlcNAc) from polypeptides. In some embodiments, a selective inhibitor of an O-GlcNAcase may selectively bind to an O-GlcNAcase. In some embodiments, a selective inhibitor of an O-GlcNAcase may inhibit hyperphosphorylation of a tau protein and/or inhibit formations of NFTs. By "inhibit," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase may elevate or enhance O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase may exhibit a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

One or more of the compounds of the present invention may elevate O-GlcNAc levels on O-GlcNAc-modified polypeptides or proteins in vivo specifically via interaction with an O-GlcNAcase enzyme, and may be effective in treating conditions which require or respond to inhibition of O-GlcNAcase activity.

In some embodiments, one or more of the compounds of the present invention may be useful as agents that produce a decrease in tau phosphorylation and NFT formation. In some embodiments, one or more of the compounds may therefore be useful to treat Alzheimer's disease and related tauopathies. In some embodiments, one or more of the compounds may thus be capable of treating Alzheimer's disease and related tauopathies by lowering tau phosphorylation and reducing NFT formation as a result of increasing tau O-GlcNAc levels. In some embodiments, one or more of the compounds may produce an increase in levels of O-GlcNAc modification on O-GlcNAc-modified polypeptides or proteins, and may therefore be useful for treatment of disorders responsive to such increases in O-GlcNAc modification; these disorders may include, without limitation, neurodegenerative, inflammatory, cardiovascular, and immunoregulatory diseases. In some embodiments, a compound may also be useful as a result of other biological activities related to its ability to inhibit the activity of glycosidase enzymes. In alternative embodiments, one or more of the compounds of the invention may be valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In specific embodiments, the invention provides compounds described generally by Formula (I) and the salts, prodrugs, and enantiomeric forms thereof:

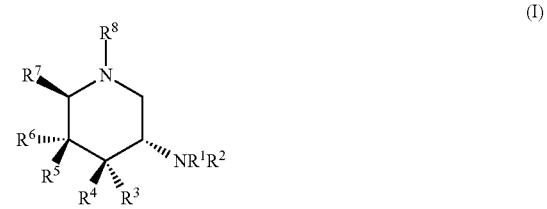

(I)

As set forth in Formula (I): $R^1$ may be H or $C_{1-6}$ alkyl; $R^2$ may be $C_{1-6}$ acyl; $R^3$ may be H and $R^4$ may be OH, or $R^3$ may be H and $R^4$ may be H, or $R^3$ may be H and $R^4$ may be F, or $R^3$ may be F and $R^4$ may be H, or $R^3$ may be F and $R^4$ may be F, or $R^3$ may be OH and $R^4$ may be H; $R^5$ may be H and $R^6$ may be OH, or $R^5$ may be H and $R^6$ may be H, or $R^5$ may be H and $R^6$ may be F, or $R^5$ may be F and $R^6$ may be H, or $R^5$ may be F and $R^6$ may be F, or $R^5$ may be OH and $R^6$ may be H; $R^7$ may be selected from the group consisting of: H, $CH_3$, $CH_2F$, $CHF_2$, and $CH_2OH$; and $R^8$ may be selected from the group consisting of: H, $C_{1-10}$ alkyl, $C_{2-10}$ alkenyl, $C_{2-10}$ alkynyl, $C_{1-10}$ acyl, $C_{8-20}$ arylalkylacyl, $C_{3-20}$ heteroarylalkylacyl, $C_{7-20}$ arylalkyl, $C_{8-20}$ arylalkenyl, $C_{8-20}$ arylalkynyl, $C_{2-20}$ heteroarylalkyl, $C_{3-20}$ heteroarylalkenyl, and $C_{3-20}$ heteroarylalkynyl, each excluding H optionally substituted from one to four substituents with one of more of halo, OH, $OCF_3$, CN, $SO_2NH_2$, $SO_2Me$, C(O)$NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

In some embodiments, $R^1$ as set forth in Formula (I) may be H or $C_{1-6}$ alkyl. In some embodiments, $R^1$ may be $CH_3$ or $CH_2CH_3$. In some embodiments, $R^1$ may be H.

In some embodiments, $R^2$ as set forth in Formula (I) may be $C_{1-6}$ acyl. In some embodiments, $R^2$ may be C(O)$CH_3$, C(O)$CH_2CH_3$, C(O)$(CH_2)_2CH_3$, or C(O)$CH(CH_3)_2$.

In some embodiments, $R^3$ as set forth in Formula (I) may be H, F, or OH. In some embodiments, $R^3$ may be H or F. In some embodiments, $R^3$ may be F.

In some embodiments, $R^4$ as set forth in Formula (I) may be H, F, or OH. In some embodiments, $R^4$ may be H or F. In some embodiments, $R^4$ may be F.

In some embodiments, $R^5$ as set forth in Formula (I) may be H, F, or OH. In some embodiments, $R^5$ may be H or F. In some embodiments, $R^5$ may be F.

In some embodiments, $R^6$ as set forth in Formula (I) may be H, F, or OH. In some embodiments, $R^6$ may be H or F. In some embodiments, $R^6$ may be F.

In some embodiments, $R^7$ as set forth in Formula (I) may be selected from the group consisting of: H, $CH_3$, $CH_2F$, $CHF_2$, and $CH_2OH$. In some embodiments, $R^7$ may be CH$_2$OH. In some embodiments, R$^7$ may be CH$_2$F or CHF$_2$. In some embodiments, R$^7$ may be CH$_3$. In some embodiments, R$^7$ may be H.

In some embodiments, R$^8$ as set forth in Formula (I) may be selected from the group consisting of: H, C$_{1-10}$ alkyl, C$_{2-10}$ alkenyl, C$_{2-10}$ alkynyl, C$_{1-10}$ acyl, C$_{8-20}$ arylalkylacyl, C$_{3-20}$ heteroarylalkylacyl, C$_{7-20}$ arylalkyl, C$_{8-20}$ arylalkenyl, C$_{8-20}$ arylalkynyl, C$_{2-20}$ heteroarylalkyl, C$_{3-20}$ heteroarylalkenyl, and C$_{3-20}$ heteroarylalkynyl, each excluding H optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl. In some embodiments, R$^8$ may be selected from the group consisting of: C$_{1-10}$ alkyl, C$_{7-20}$ arylalkyl, and C$_{2-20}$ heteroarylalkyl, each optionally substituted from one to four substituents with one of more of halo, OH, OCF$_3$, CN, SO$_2$NH$_2$, SO$_2$Me, C(O)NH$_2$, CH$_2$F, CHF$_2$, CF$_3$, CH$_2$CH$_2$F, CH$_2$CF$_3$, CH$_2$CH$_2$CH$_2$F, C$_{1-6}$ alkyl, C$_{1-6}$ alkoxy, or C$_{3-7}$ cycloalkyl. In some embodiments, R$^8$ may be selected from the group consisting of: H, CH$_3$, hexyl, (CH$_2$)$_2$(phenyl), (CH$_2$)$_3$(phenyl), (CH$_2$)$_4$(phenyl), 3-phenylpropanoyl, 3-(6-fluoropyridin-3-yl)propyl, 4,4,4-trifluorobutyl, 3-(5-(trifluoromethoxy)benzo[d]thiazol-2-yl)propyl, (Z)-5,5,5-trifluoropent-3-en-1-yl, pent-4-yn-1-yl, butyryl, 3-(6-fluoropyridin-3-yl)propanoyl, cinnamyl, 3-phenylprop-2-yn-1-yl, (E)-3-(6-fluoropyridin-3-yl)allyl, and 3-(6-fluoropyridin-3-yl)prop-2-yn-1-yl.

In specific embodiments of the invention, compounds according to Formula (I) include the compounds described in Table 1.

TABLE 1

| Example | Name | Structure |
|---|---|---|
| 1 | N-((3S,4R,5R,6R)-4,5-dihydroxy-6-(hydroxymethyl)-1-(4-phenylbutyl)piperidin-3-yl)acetamide | 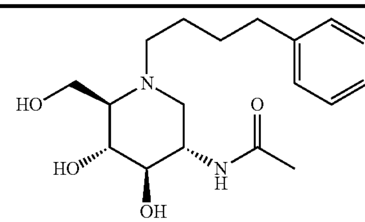 |
| 2 | N-((3S,4R,5R)-1-hexyl-4,5-dihydroxypiperidin-3-yl)acetamide | 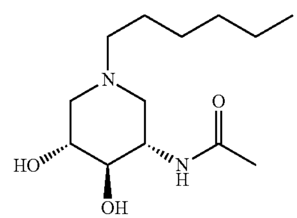 [SMILES: CCCCCCN1C[C@@H](O)[C@H](O)[C@@H](NC(C)=O)C1] |
| 3 | N-((3S,4R,5R,6R)-4,5-dihydroxy-6-(hydroxymethyl)-1-phenethylpiperidin-3-yl)propionamide | 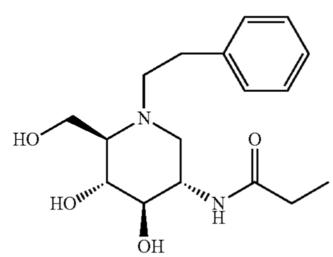 [SMILES: CCC(=O)N[C@H]1CN(CCc2ccccc2)[C@H](CO)[C@@H](O)[C@@H]1O] |
| 4 | N-((3S,4R,5R,6S)-6-(fluoromethyl)-4,5-dihydroxy-1-phenethylpiperidin-3-yl)propionamide | 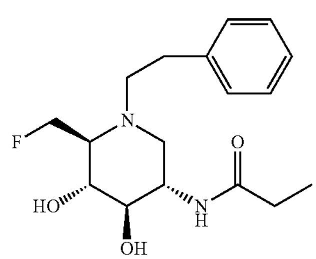 [SMILES: CCC(=O)N[C@H]1CN(CCc2ccccc2)[C@H](CF)[C@@H](O)[C@@H]1O] |
| 5 | N-((3S,4R,5R,6R)-4-fluoro-5-hydroxy-6-(hydroxymethyl)-1-phenethylpiperidin-3-yl)propionamide | 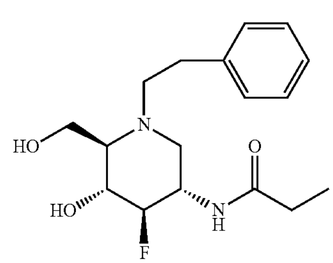 [SMILES: CCC(=O)N[C@H]1CN(CCc2ccccc2)[C@H](CO)[C@@H](O)[C@@H]1F] |

TABLE 1-continued

| Example | Name | Structure |
|---|---|---|
| 6 | N-((3S,4R,5R,6S)-6-(difluoromethyl)-4,5-dihydroxy-1-phenethylpiperidin-3-yl)propionamide | 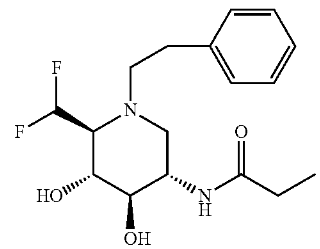 [SMILES: CCC(=O)N[C@H]1CN(CCc2ccccc2)[C@H](C(F)F)[C@@H](O)[C@@H]1O] |
| 7 | N-((3S,4R,5R,6R)-4,5-dihydroxy-6-(hydroxymethyl)-1-(3-phenylpropyl)piperidin-3-yl)propionamide | 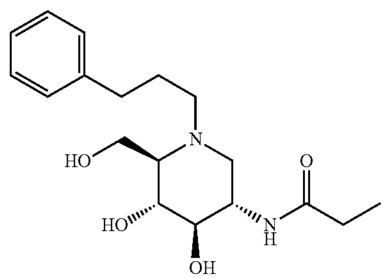 [SMILES: CCC(=O)N[C@H]1CN(CCCc2ccccc2)[C@H](CO)[C@@H](O)[C@@H]1O] |
| 8 | N-((3S,4R,5R,6R)-4-fluoro-5-hydroxy-6-(hydroxymethyl)-1-(3-phenylpropyl)piperidin-3-yl)propionamide | 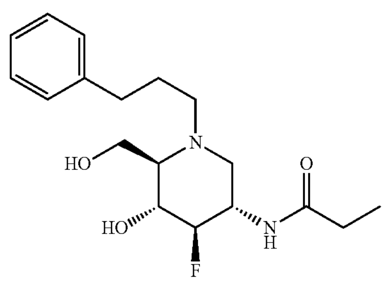 [SMILES: CCC(=O)N[C@H]1CN(CCCc2ccccc2)[C@H](CO)[C@@H](O)[C@@H]1F] |
| 9 | N-((3S,4R,5R,6R)-5-fluoro-4-hydroxy-6-(hydroxymethyl)-1-(3-phenylpropyl)piperidin-3-yl)propionamide | 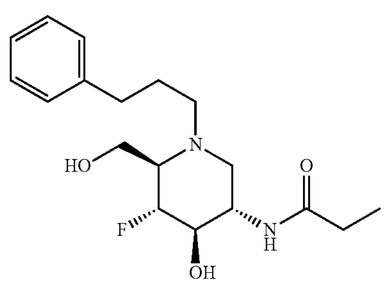 [SMILES: CCC(=O)N[C@H]1CN(CCCc2ccccc2)[C@H](CO)[C@@H](F)[C@@H]1O] |
| 10 | N-((3S,4R,5R,6S)-6-(fluoromethyl)-4,5-dihydroxy-1-(3-phenylpropyl)piperidin-3-yl)propionamide | 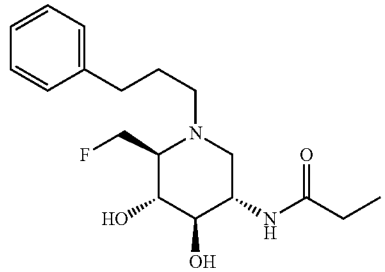 [SMILES: CCC(=O)N[C@H]1CN(CCCc2ccccc2)[C@H](CF)[C@@H](O)[C@@H]1O] |

TABLE 1-continued

| Example | Name | Structure |
|---|---|---|
| 11 | N-((3S,4S,5R,6R)-4-fluoro-5-hydroxy-6-(hydroxymethyl)-1-(3-phenylpropyl)piperidin-3-yl)propionamide | 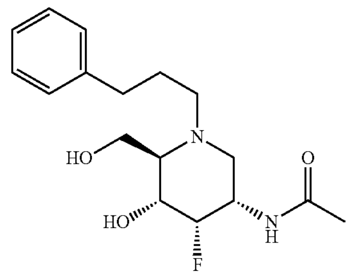 [SMILES: CC(=O)N[C@H]1CN(CCCc2ccccc2)[C@H](CO)[C@@H](O)[C@H]1F] |
| 12 | N-((3S,4R,5S,6R)-5-fluoro-4-hydroxy-6-(hydroxymethyl)-1-(3-phenylpropyl)piperidin-3-yl)propionamide | 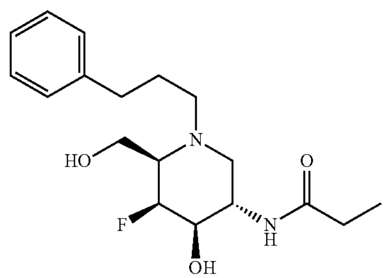 [SMILES: CCC(=O)N[C@H]1CN(CCCc2ccccc2)[C@H](CO)[C@H](F)[C@@H]1O] |
| 13 | N-((3S,4R,5R,6S)-6-(difluoromethyl)-4,5-dihydroxy-1-(3-phenylpropyl)piperidin-3-yl)propionamide | 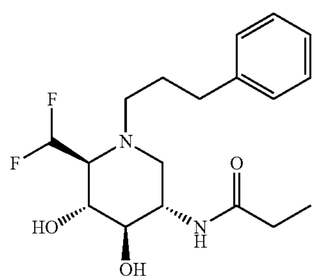 [SMILES: CCC(=O)N[C@H]1CN(CCCc2ccccc2)[C@H](C(F)F)[C@@H](O)[C@@H]1O] |
| 14 | N-((3S,4R,5R,6S)-6-(difluoromethyl)-4-fluoro-5-hydroxy-1-(3-phenylpropyl)piperidin-3-yl)propionamide | 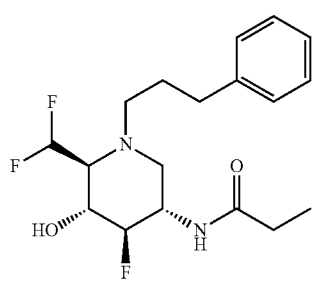 [SMILES: CCC(=O)N[C@H]1CN(CCCc2ccccc2)[C@H](C(F)F)[C@@H](O)[C@@H]1F] |
| 15 | N-((3S,4S,5R,6S)-6-(difluoromethyl)-4-fluoro-5-hydroxy-1-(3-phenylpropyl)piperidin-3-yl)propionamide | 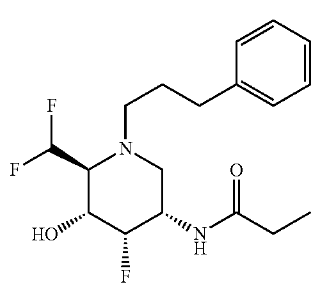 [SMILES: CCC(=O)N[C@H]1CN(CCCc2ccccc2)[C@H](C(F)F)[C@@H](O)[C@H]1F] |

TABLE 1-continued

| Example | Name | Structure |
|---|---|---|
| 16 | N-((3R,5S,6R)-5-hydroxy-6-(hydroxymethyl)-1-(3-phenylpropyl)piperidin-3-yl)propionamide | 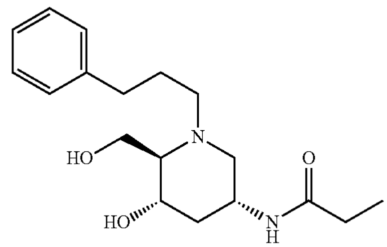 [SMILES: CCC(=O)N[C@@H]1C[C@H](O)[C@@H](CO)N(CCCc2ccccc2)C1] |
| 17 | N-((3S,4S,6S)-4-hydroxy-6-(hydroxymethyl)-1-(3-phenylpropyl)piperidin-3-yl)propionamide | 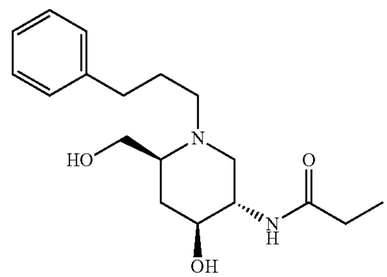 [SMILES: CCC(=O)N[C@H]1CN(CCCc2ccccc2)[C@H](CO)C[C@@H]1O] |
| 18 | N-((3S,4R,5R,6R)-4,5-dihydroxy-6-methyl-1-(3-phenylpropyl)piperidin-3-yl)propionamide | 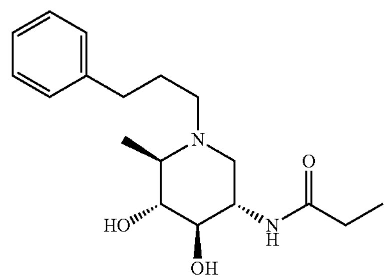 [SMILES: CCC(=O)N[C@H]1CN(CCCc2ccccc2)[C@H](C)[C@@H](O)[C@@H]1O] |
| 19 | N-((3S,4R,5R)-4,5-dihydroxy-1-(3-phenylpropyl)piperidin-3-yl)propionamide | 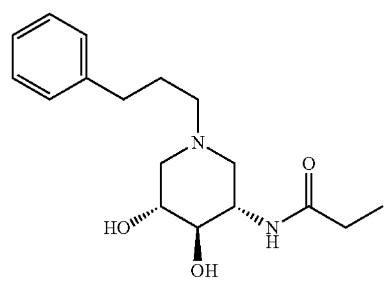 [SMILES: CCC(=O)N[C@H]1CN(CCCc2ccccc2)C[C@@H](O)[C@@H]1O] |
| 20 | N-((3S,4R,5R)-4-fluoro-5-hydroxy-1-(3-phenylpropyl)piperidin-3-yl)propionamide | 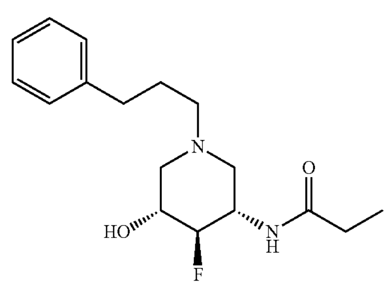 [SMILES: CCC(=O)N[C@H]1CN(CCCc2ccccc2)C[C@@H](O)[C@@H]1F] |

TABLE 1-continued

| Example | Name | Structure |
|---|---|---|
| 21 | N-((3S,4R,5R,6R)-4,5-dihydroxy-6-(hydroxymethyl)-1-(3-phenylpropanoyl)piperidin-3-yl)propionamide | 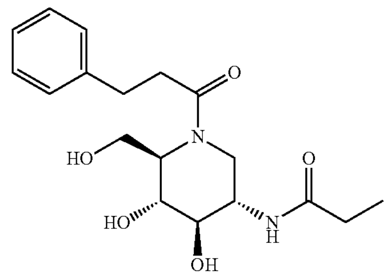 [SMILES: CCC(=O)N[C@H]1CN(C(=O)CCc2ccccc2)[C@H](CO)[C@@H](O)[C@@H]1O] |
| 22 | N-((3S,4R,5R,6R)-1-(3-(6-fluoropyridin-3-yl)propyl)-4,5-dihydroxy-6-(hydroxymethyl)piperidin-3-yl)propionamide | 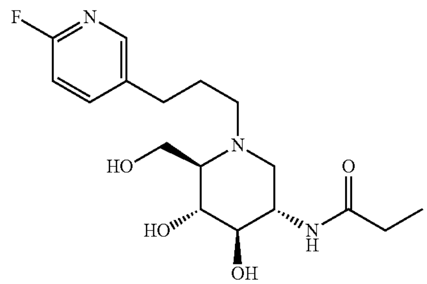 [SMILES: CCC(=O)N[C@H]1CN(CCCc2ccc(F)nc2)[C@H](CO)[C@@H](O)[C@@H]1O] |
| 23 | N-((3S,4R,5R,6R)-4,5-dihydroxy-6-(hydroxymethyl)-1-(4,4,4-trifluorobutyl)piperidin-3-yl)propionamide | 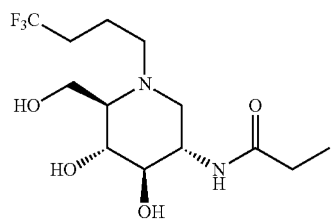 [SMILES: CCC(=O)N[C@H]1CN(CCCC(F)(F)F)[C@H](CO)[C@@H](O)[C@@H]1O] |
| 24 | N-((3S,4R,5R,6R)-4,5-dihydroxy-6-(hydroxymethyl)-1-(3-(5-(trifluoromethoxy)benzo+d+thiazol-2-yl)propyl)piperidin-3-yl)propionamide | 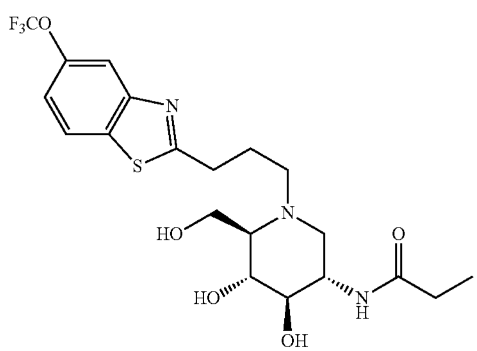 [SMILES: CCC(=O)N[C@H]1CN(CCCc2nc3cc(OC(F)(F)F)ccc3s2)[C@H](CO)[C@@H](O)[C@@H]1O] |
| 25 | N-((3S,4R,5R,6R)-4,5-dihydroxy-6-(hydroxymethyl)-1-((Z)-5,5,5-trifluoropent-3-en-1-yl)piperidin-3-yl)propionamide | 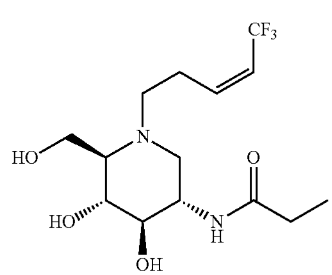 [SMILES: CCC(=O)N[C@H]1CN(CC/C=C\C(F)(F)F)[C@H](CO)[C@@H](O)[C@@H]1O] |

TABLE 1-continued

| Example | Name | Structure |
|---|---|---|
| 26 | N-((3S,4R,5R,6R)-4,5-dihydroxy-6-(hydroxymethyl)-1-(pent-4-yn-1-yl)piperidin-3-yl)propionamide | 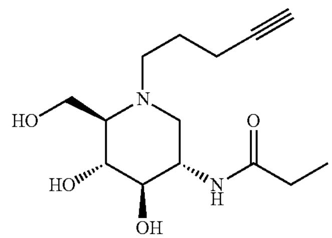 [SMILES: C#CCCCN1C[C@H](NC(=O)CC)[C@@H](O)[C@H](O)[C@H]1CO] |
| 27 | N-((3S,4R,5R,6R)-1-butyryl-4,5-dihydroxy-6-(hydroxymethyl)piperidin-3-yl)propionamide | 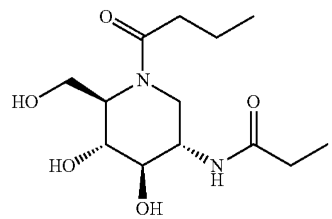 [SMILES: CCCC(=O)N1C[C@H](NC(=O)CC)[C@@H](O)[C@H](O)[C@H]1CO] |
| 28 | N-((3S,4R,5R,6R)-1-(3-(6-fluoropyridin-3-yl)propanoyl)-4,5-dihydroxy-6-(hydroxymethyl)piperidin-3-yl)propionamide | 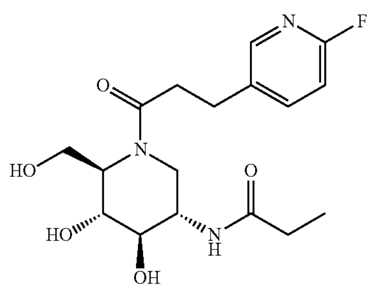 [SMILES: CCC(=O)N[C@H]1CN(C(=O)CCc2ccc(F)nc2)[C@H](CO)[C@@H](O)[C@@H]1O] |
| 29 | N-((3S,4R,5R,6R)-1-cinnamyl-4,5-dihydroxy-6-(hydroxymethyl)piperidin-3-yl)propionamide | 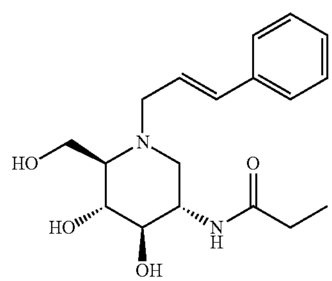 [SMILES: CCC(=O)N[C@H]1CN(C/C=C/c2ccccc2)[C@H](CO)[C@@H](O)[C@@H]1O] |
| 30 | N-((3S,4R,5R,6R)-4,5-dihydroxy-6-(hydroxymethyl)-1-(3-phenylprop-2-yn-1-yl)piperidin-3-yl)propionamide | 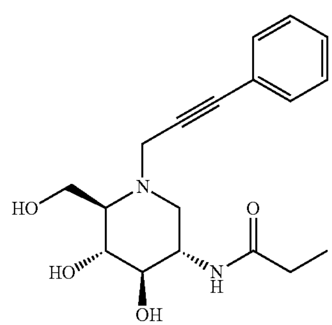 [SMILES: CCC(=O)N[C@H]1CN(CC#Cc2ccccc2)[C@H](CO)[C@@H](O)[C@@H]1O] |

TABLE 1-continued

| Example | Name | Structure |
|---|---|---|
| 31 | N-((3S,4R,5R,6R)-1-((E)-3-(6-fluoropyridin-3-yl)allyl)-4,5-dihydroxy-6-(hydroxymethyl)piperidin-3-yl)propionamide | 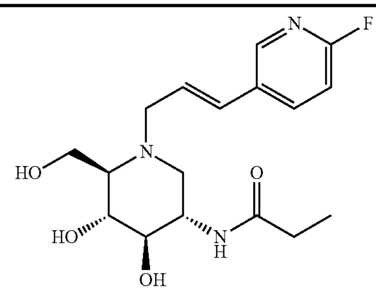 |
| 32 | N-((3S,4R,5R,6R)-1-(3-(6-fluoropyridin-3-yl)prop-2-yn-1-yl)-4,5-dihydroxy-6-(hydroxymethyl)piperidin-3-yl)propionamide | 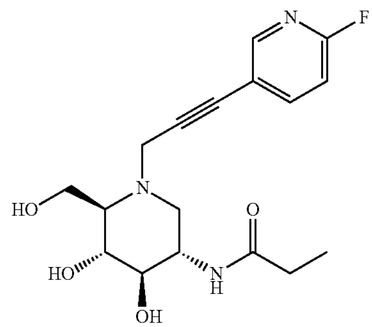 [SMILES: CCC(=O)N[C@H]1CN(CC#Cc2ccc(F)nc2)[C@H](CO)[C@@H](O)[C@@H]1O] |

In alternative embodiments of the invention, compounds according to Formula (I) include one or more of the compounds described in Table 2.

In alternative embodiments of the invention, one or more of the compounds described in Table 2 are specifically excluded from the compounds described in Formula (I).

TABLE 2

| Name | Structure |
|---|---|
| N-((3S,4R,5R,6R)-4,5-dihydroxy-6-(hydroxymethyl)piperidin-3-yl)acetamide | 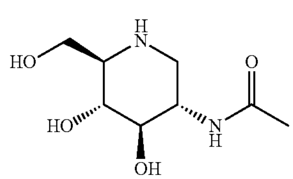 |
| N-((3S,4R,5S,6R)-4,5-dihydroxy-6-(hydroxymethyl)piperidin-3-yl)acetamide | 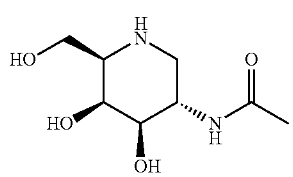 |
| N-((3S,4R,5R,6R)-4,5-dihydroxy-6-(hydroxymethyl)-1-methylpiperidin-3-yl)acetamide | 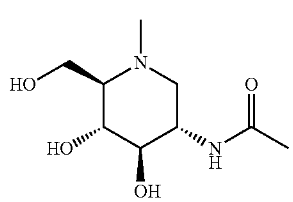 |
| N-((3S,4R,5R,6R)-1-butyl-4,5-dihydroxy-6-(hydroxymethyl)piperidin-3-yl)acetamide | |
| N-((3S,4R,5R,6R)-1-benzyl-4,5-dihydroxy-6-(hydroxymethyl)piperidin-3-yl)acetamide | |
| N-((3S,4R,5R,6R)-1-butyl-4,5-dihydroxy-6-(hydroxymethyl)piperidin-3-yl)butyramide | |

TABLE 2-continued

| Name | Structure |
|---|---|
| N-((3S,4R,5R,6R)-1-(5-cyanopentyl)-4,5-dihydroxy-6-(hydroxymethyl)piperidin-3-yl)acetamide | 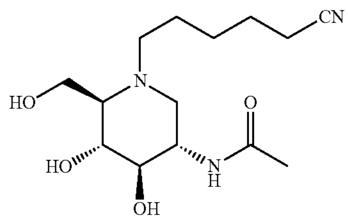 [SMILES: CC(=O)N[C@H]1CN(CCCCCC#N)[C@H](CO)[C@@H](O)[C@@H]1O] |
| N-((3S,4R,5R,6R)-1-benzhydryl-4,5-dihydroxy-6-(hydroxymethyl)piperidin-3-yl)acetamide | 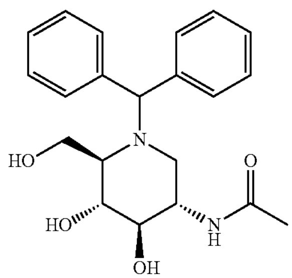 [SMILES: CC(=O)N[C@H]1CN(C(c2ccccc2)c2ccccc2)[C@H](CO)[C@@H](O)[C@@H]1O] |
| N-((3S,4R,5R,6R)-4,5-dihydroxy-6-methylpiperidin-3-yl)acetamide | 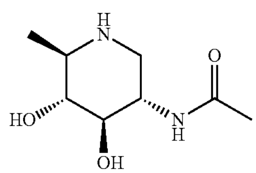 |
| N-((3S,4R,5R,6R)-1-acetyl-4,5-dihydroxy-6-methylpiperidin-3-yl)acetamide | 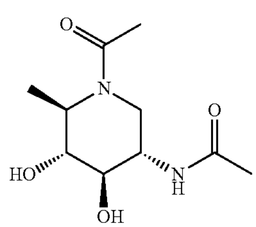 [SMILES: CC(=O)N[C@H]1CN(C(C)=O)[C@H](C)[C@@H](O)[C@@H]1O] |
| N-((3S,4R,5R)-4,5-dihydroxypiperidin-3-yl)acetamide | 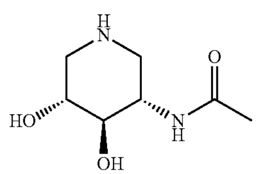 |
| N-((3S,4R,5S)-4,5-dihydroxypiperidin-3-yl)acetamide | 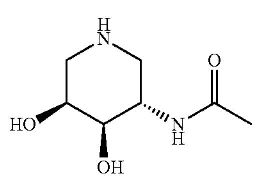 |
| N-((3S,4S,5R)-4,5-dihydroxypiperidin-3-yl)acetamide | 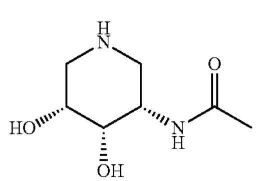 |
| N-((3S,4R,5R)-4,5-dihydroxy-1-methylpiperidin-3-yl)acetamide | |
| N-((3S,4S,5R)-4,5-dihydroxy-1-methylpiperidin-3-yl)acetamide | |
| N-((3S,4R,5S)-4,5-dihydroxy-1-methylpiperidin-3-yl)acetamide | |
| N-((3S,4R,5R)-1-butyl-4,5-dihydroxypiperidin-3-yl)acetamide | |
| N-((3S,4R,5S)-1-butyl-4,5-dihydroxypiperidin-3-yl)acetamide | |
| N-((3S,4S,5R)-1-butyl-4,5-dihydroxypiperidin-3-yl)acetamide | |
| N-((3S,4R,5R)-4,5-dihydroxy-1-nonylpiperidin-3-yl)acetamide | |

TABLE 2-continued

| Name | Structure |
|---|---|
| N-((3S,4S,5R)-4,5-dihydroxy-1-nonylpiperidin-3-yl)acetamide | 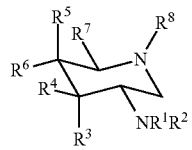 |

In alternative embodiments of the invention, compounds according to Formula (I) include one or more of the compounds described in Table 2 in which one or more OH groups are replaced by F or H.

In alternative embodiments of the invention, one or more of the compounds described in Table 2 in which one or more OH groups is replaced by F or H are specifically excluded from the compounds described in Formula (I).

As will be appreciated by a person skilled in the art, Formula (I) above may also be represented alternatively as follows:

$$\begin{array}{c} R^5 \\ R^7 \\ R^6 \\ R^4 \\ R^3 \end{array} \begin{array}{c} R^8 \\ N \\ NR^1R^2 \end{array}$$

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. In alternative embodiments, the alkenyl group may contain from two to eight carbon atoms, such as 2, 3, 4, 5, 6, 7, or 8 carbon atoms. In alternative embodiments, the alkenyl group may contain from three to six carbon atoms, such as 3, 4, 5, or 6 carbon atoms. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. In alternative embodiments, the alkynyl group may contain from two to eight carbon atoms, such as 2, 3, 4, 5, 6, 7, or 8 carbon atoms. In alternative embodiments, the alkynyl group may contain from three to six carbon atoms, such as 3, 4, 5, or 6 carbon atoms. Unless stated otherwise specifically in the specification, the alkynyl group may be optionally substituted by one or more substituents as described herein.

"Aryl" refers to a mono- or bicyclic aromatic ring containing only carbon atoms, including for example, 6-14 members, such as 6, 7, 8, 9, 10, 11, 12, 13, or 14 members. Examples of aryl groups include phenyl, biphenyl, naphthyl, indanyl, indenyl, tetrahydronaphthyl, 2,3-dihydrobenzofuranyl, dihydrobenzopyranyl, 1,4-benzodioxanyl, and the like. Unless stated otherwise specifically herein, the term "aryl" is meant to include aryl groups optionally substituted by one or more substituents as described herein.

"Heteroaryl" refers to a single or fused aromatic ring group containing one or more heteroatoms in the ring, for example N, O, S, including for example, 5-14 members, such as 5, 6, 7, 8, 9, 10, 11, 12, 13, or 14 members. Examples of heteroaryl groups include furan, thiophene, pyrrole, oxazole, thiazole, imidazole, pyrazole, isoxazole, isothiazole, 1,2,3-oxadiazole, 1,2,3-triazole, 1,2,4-triazole, 1,3,4-thiadiazole, tetrazole, pyridine, pyridazine, pyrimidine, pyrazine, 1,3,5-triazine, imidazole, benzimidazole, benzoxazole, benzothiazole, indolizine, indole, isoindole, benzofuran, benzothiophene, 1H-indazole, purine, 4H-quinolizine, quinoline, isoquinoline, cinnoline, phthalazine, quinazoline, quinoxaline, 1,8-naphthyridine, pteridine, and the like. Unless stated otherwise specifically herein, the term "heteroaryl" is meant to include heteroaryl groups optionally substituted by one or more substituents as described herein.

"Arylalkyl" refers to a group of the formula —$R_aR_b$ where $R_a$ is a $C_{1-10}$ alkyl group as described herein and $R_b$ is one or more aryl moieties as described herein. The aryl group(s) may be optionally substituted as described herein.

"Arylalkenyl" refers to a group of the formula —$R_cR_b$ where $R_c$ is a $C_{2-10}$ alkenyl group as described herein and $R_b$ is one or more aryl moieties as described herein. The aryl group(s) may be optionally substituted as described herein.

"Arylalkynyl" refers to a group of the formula —$R_dR_b$ where $R_d$ is a $C_{2-10}$ alkynyl group as described herein and $R_b$ is one or more aryl moieties as described herein. The aryl group(s) may be optionally substituted as described herein.

"Heteroarylalkyl" refers to a group of the formula —$R_aR_e$ where $R_a$ is a $C_{1-10}$ alkyl group as described herein and $R_e$ is one or more heteroaryl moieties as described herein. The aryl group(s) may be optionally substituted as described herein.

"Heteroarylalkenyl" refers to a group of the formula —$R_dR_e$ where $R_d$ is a $C_{2-10}$ alkenyl group as described herein and $R_e$ is one or more heteroaryl moieties as described herein. The heteroaryl group(s) may be optionally substituted as described herein.

"Heteroarylalkynyl" refers to a group of the formula —$R_dR_e$ where $R_d$ is a $C_{2-10}$ alkynyl group as described herein and $R_e$ is one or more heteroaryl moieties as described herein. The heteroaryl group(s) may be optionally substituted as described herein.

"Acyl" refers to a group of the formula —$C(O)R_f$, where $R_f$ is H or a $C_{1-10}$ alkyl group or a $C_{1-6}$ alkyl group or a $C_{3-15}$ cycloalkyl group as described herein. The alkyl or cycloalkyl group(s) may be optionally substituted as described herein.

"Arylalkylacyl" refers to a group of the formula —$C(O)R_gR_b$, where $R_g$ is a $C_{1-10}$ alkyl or a $C_{1-6}$ alkyl group as described herein and $R_b$ is one or more aryl moieties as described herein. The alkyl or aryl group(s) may be optionally substituted as described herein.

"Heteroarylalkylacyl" refers to a group of the formula —$C(O)R_gR_e$, where $R_g$ is a $C_{1-10}$ alkyl or a $C_{1-6}$ alkyl group as described herein and $R_e$ is one or more heteroaryl moieties as described herein. The alkyl or heteroaryl group(s) may be optionally substituted as described herein.

"Alkoxy" refers to a group of the formula —$OR_g$, where $R_g$ is a $C_{1-10}$ alkyl or a $C_{1-6}$ alkyl group as described herein. The alkyl group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. In alternative embodiments, the cycloalkyl group may contain from three to six carbon atoms, such as 3, 4, 5, or 6 carbon atoms. Unless otherwise stated specifically herein, the term "cycloalkyl" is meant to include cycloalkyl groups which are optionally substituted as described herein.

"Halo" refers to bromo, chloro, fluoro, iodo, etc. In some embodiments, suitable halogens include fluorine or chlorine.

"Optional" or "optionally" means that the subsequently described event of circumstances may or may not occur, and that the description includes instances where said event or circumstance occurs one or more times and instances in which it does not. For example, "optionally substituted alkyl" means that the alkyl group may or may not be substituted and that the description includes both substituted alkyl groups and alkyl groups having no substitution, and that said alkyl groups may be substituted one or more times. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions may include, without limitation, Glaucoma, Schizophrenia, tauopathies, such as Alzheimer's disease, neurodegenerative diseases, cardiovascular diseases, diseases associated with inflammation, diseases associated with immunosuppression and cancers. One or more of the compounds of the invention may also be useful in the treatment of diseases or disorders related to deficiency or over-expression of O-GlcNAcase or accumulation or depletion of O-GlcNAc, or any disease or disorder responsive to glycosidase inhibition therapy. Such diseases and disorders may include, but are not limited to, Glaucoma, Schizophrenia, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification may result in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels may be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

In general, the methods of the invention may be effected by administering a compound according to the invention to a subject in need thereof, or by contacting a cell or a sample with a compound according to the invention, for example, a pharmaceutical composition comprising a therapeutically effective amount of the compound according to Formula (I). More particularly, they may be useful in the treatment of a disorder in which the regulation of O-GlcNAc protein modification is implicated, or any condition as described herein. Disease states of interest may include Alzheimer's disease (AD) and related neurodegenerative tauopathies, in which abnormal hyperphosphorylation of the microtubule-associated protein tau is involved in disease pathogenesis. In some embodiments, a compound may be used to block hyperphosphorylation of tau by maintaining elevated levels of O-GlcNAc on tau, thereby providing therapeutic benefit.

The effectiveness of a compound in treating pathology associated with the accumulation of toxic tau species (for example, Alzheimer's disease and other tauopathies) may be confirmed by testing the ability of a compound to block the formation of toxic tau species in established cellular[121-123] and/or transgenic animal models of disease.[33,34]

Tauopathies that may be treated with a compound of the invention may include, without limitation: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention may also be useful in the treatment of conditions associate with tissue damage or stress, stimulating cells, or promoting differentiation of cells. Accordingly, in some embodiments, a compound of this invention may be used to provide therapeutic benefit in a variety of conditions or medical procedures involving stress in cardiac tissue; such conditions may include, without limitation: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays,[108,119,120] and to prevent tissue damage and promote functional recovery in animal models of ischemia-reperfusion,[71,117] and trauma-hemorrhage.[73,115,118]

Compounds that selectively inhibit O-GlcNAcase activity may be used for the treatment of diseases that are associated with inflammation; such conditions may include, without limitation: inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myasthenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affect levels of protein O-GlcNAc modification may be used for the treatment of diseases associated with immunosuppression, such as, for example, in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegenerative diseases; such conditions may include, without limitation, Parkinson's disease and Huntington's disease. Other conditions that may be treated are those triggered, affected, or in any other way correlated with levels of O-GlcNAc post-translational protein modification. It is expected that one or more of the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I) are provided.

The compounds of Formula (I) and their pharmaceutically acceptable salts, enantiomers, solvates, and derivatives may be useful because they may have pharmacological activity in animals, including humans. In some embodiments, one or more of the compounds according to the invention may be stable in plasma, when administered to a subject.

In some embodiments, a compound according to the invention, or for use according to the invention, may be provided in combination with any other active agents or pharmaceutical compositions where such combined therapy may be useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents may include, without limitation, acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda® (Axura®, Akatinol®, Ebixa®, Memantine), Dimebon, SGS-742, Neramexane, Debio-9902 SR (ZT-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-Z1, CTS-21166, MK-8931, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfurindamide, LiCl, AZD1080, NP031112, SAR-502250, etc.

humanized monoclonal anti-Aβ antibodies such as Bapineuzumab (AAB-001), LY2062430, RN1219, ACU-5A5, etc.;

amyloid vaccines such as AN-1792, ACC-001, etc.;

neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but may include combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, a compound may be supplied as a "prodrug" or protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but may be converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987.

Suitable prodrug forms of one or more of the compounds of the invention may include embodiments in which one or more OH groups as set forth in Formula (I) may be protected as OC(O)R, where R may be optionally substituted alkyl, alkenyl, alkynyl, aryl, or heteroaryl. In these cases the ester groups may be hydrolyzed in vivo (e.g. in bodily fluids), liberating the OH groups and releasing the active compounds. Preferred prodrug embodiments of the invention may include compounds of Formula (I) where one or more OH groups may be protected with acetate, for example as $OC(O)CH_3$.

Compounds according to the invention, or for use according to the invention, may be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartrate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes.

Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require modulation of O-GlcNAcase activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 µM or 0.01 nM-10 µM.

In alternative embodiments, in the treatment or prevention of conditions which may require modulation of O-GlcNAcase activity, an appropriate dosage level may generally be about 0.01 to 500 mg per kg subject body weight per day, and may be administered in singe or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1H$), deuterium ($^2H$) and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) may be prepared without undue experimentation by conventional techniques well known to those skilled in the art or by processes analogous to those described in the Schemes and Examples herein using appropriate isotopically-enriched reagents and/or intermediates.

Other Uses and Assays

A compound of Formula (I) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluorescence or UV-based assay known in the art may be used. A "test compound" may be any naturally-occurring or artificially-derived chemical compound. Test compounds may include, without limitation, peptides, polypeptides, synthesised organic molecules, naturally occurring organic molecules, and nucleic acid molecules. A test compound may "compete" with a known compound such as a compound of Formula (I) by, for example, interfering with inhibition of O-GlcNAcase-dependent cleavage of O-GlcNAc or by interfering with any biological response induced by a compound of Formula (I).

Generally, a test compound may exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator may in general decrease modulation relative to a known compound, while a compound that is a positive modulator may in general increase modulation relative to a known compound.

In general, test compounds may be identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds may be screened using the exemplary methods described herein. Examples of such extracts or compounds may include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, that may include, without limitation, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries may be produced, if desired, according to methods known in the art, e.g., by standard extraction and fractionation methods. Furthermore, if desired, any library or compound may be readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract may be necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds may be used to purify the active component and to test derivatives thereof. Methods of fractionation and purification of such heterogeneous extracts are known in the art. If desired, compounds shown to be useful agents for treatment may be chemically modified according to methods known in the art. Compounds identified as being of therapeutic, prophylactic, diagnostic, or other value may be subsequently analyzed using a suitable animal model, as described herein on known in the art.

In some embodiments, one or more of the compounds may be useful in the development of animal models for studying diseases or disorders that may be related to deficiencies in O-GlcNAcase, over-expression of O-GlcNAcase, accumulation of O-GlcNAc, depletion of O-GlcNAc, and for studying treatment of diseases and disorders that may be related to deficiency or over-expression of O-GlcNAcase, or accumulation or depletion of O-GlcNAc. Such diseases and disorders may include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations

ABCN=1,1'-azobis(cyclohexane-carbonitrile)
AcCl=acetyl chloride
AIBN=azobisisobutyronitrile
$BCl_3$=boron trichloride
BnBr=benzyl bromide
$Bu_4NI$=tetra-n-butylammonium iodide
$Boc_2O$=di-tert-butyl dicarbonate
BzCl=benzoyl chloride
DAST=diethylaminosulfur trifluoride
DCM=dichloromethane
DIAD=diisopropyl azodicarboxylate
DIPEA=diisopropylethylamine
DMAP=4-dimethylaminopyridine
DMF=N,N-dimethylformamide
DMP=Dess-Martin periodinane
DMSO=dimethyl sulfoxide
EDCI=1-ethyl-3-(3-dimethylaminopropyl)carbodiimide
$Et_3N$=triethylamine
$Et_2O$=diethyl ether HATU=(O-(7-azabenzotriazol-1-yl)-N,N,N',N'-tetramethyluronium hexafluorophosphate)
PMB=pentamethylbenzene
TBDMSCl=tert-butyldimethylsilyl chloride
TBAF=tetra-n-butylammonium fluoride
TMSCF₃=(trifluoromethyl)trimethylsilane
TFA=2,2,2-trifluoroacetic acid
THF=tetrahydrofuran
thio-CDI=1,1'-thiocarbonyl diimidazole General Procedures and Intermediates The compounds of the invention are synthesized according to standard schemes and procedures, as indicated in, for example, Schemes 1 to 9, as appropriate. Intermediate A (Scheme 1) may be prepared as described in, for example, PCT WO 2006/008194. Intermediate B (Scheme 5) may be prepared as described in, for example, *Carb. Res.* 1987, 167, 312. For Schemes 1 to 9, the general procedures are defined as follows:

General procedure A: Pd(OH)₂/H₂, MeOH, 50° C., 50 psi
General Procedure B: RCHO, NaBH₃CN, HOAc, MeOH
General Procedure C: 4N HCl, 40° C.
General Procedure D: RCOOH, HATU, DMF, i-Pr₂NEt
General Procedure E: RBr, K₂CO₃, DMF It is to be understood that any suitable scheme within the knowledge of one skilled in the art may be used to synthesize one or more of the compounds described herein.

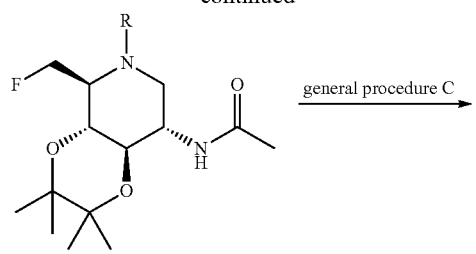
general procedure C
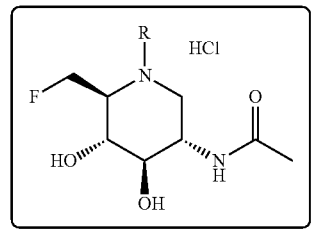
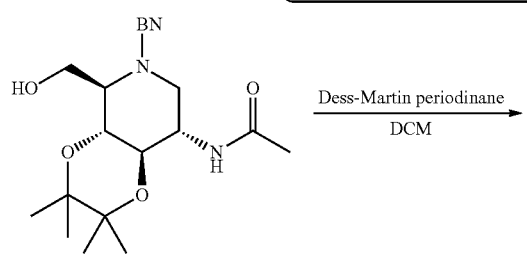
Dess-Martin periodinane
DCM
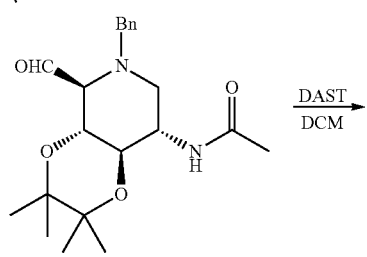
DAST
DCM
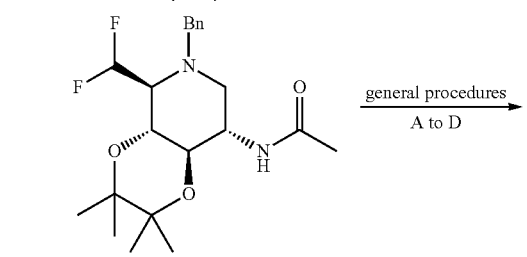
general procedures
A to D
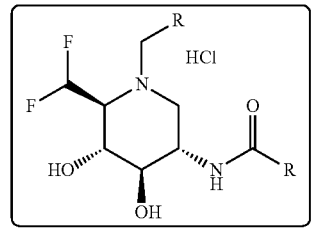
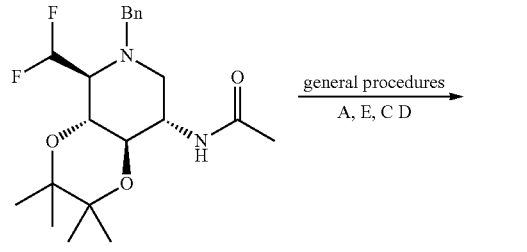
general procedures
A, E, C D
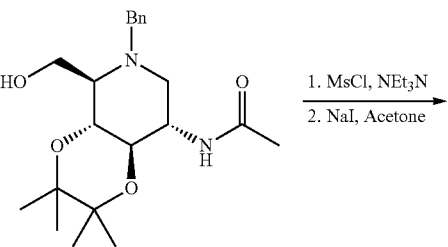
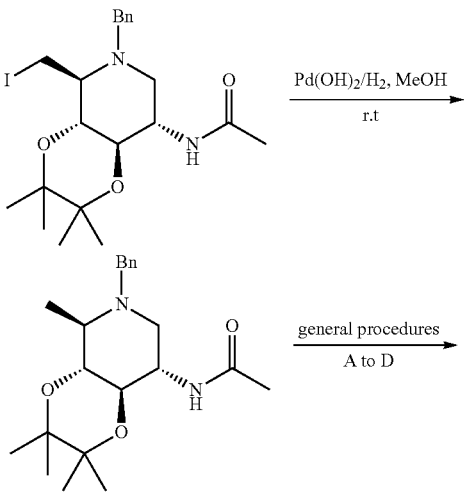
1. MsCl, NEt₃N
2. NaI, Acetone
Pd(OH)₂/H₂, MeOH
r.t
general procedures
A to D
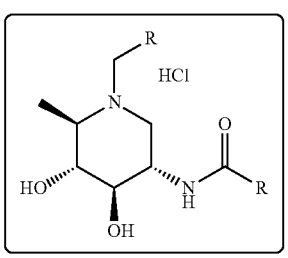
general procedures
A, E, C, D
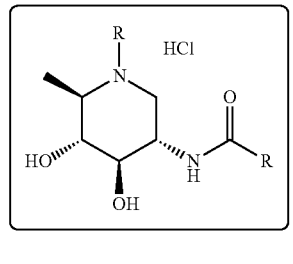

Scheme 2
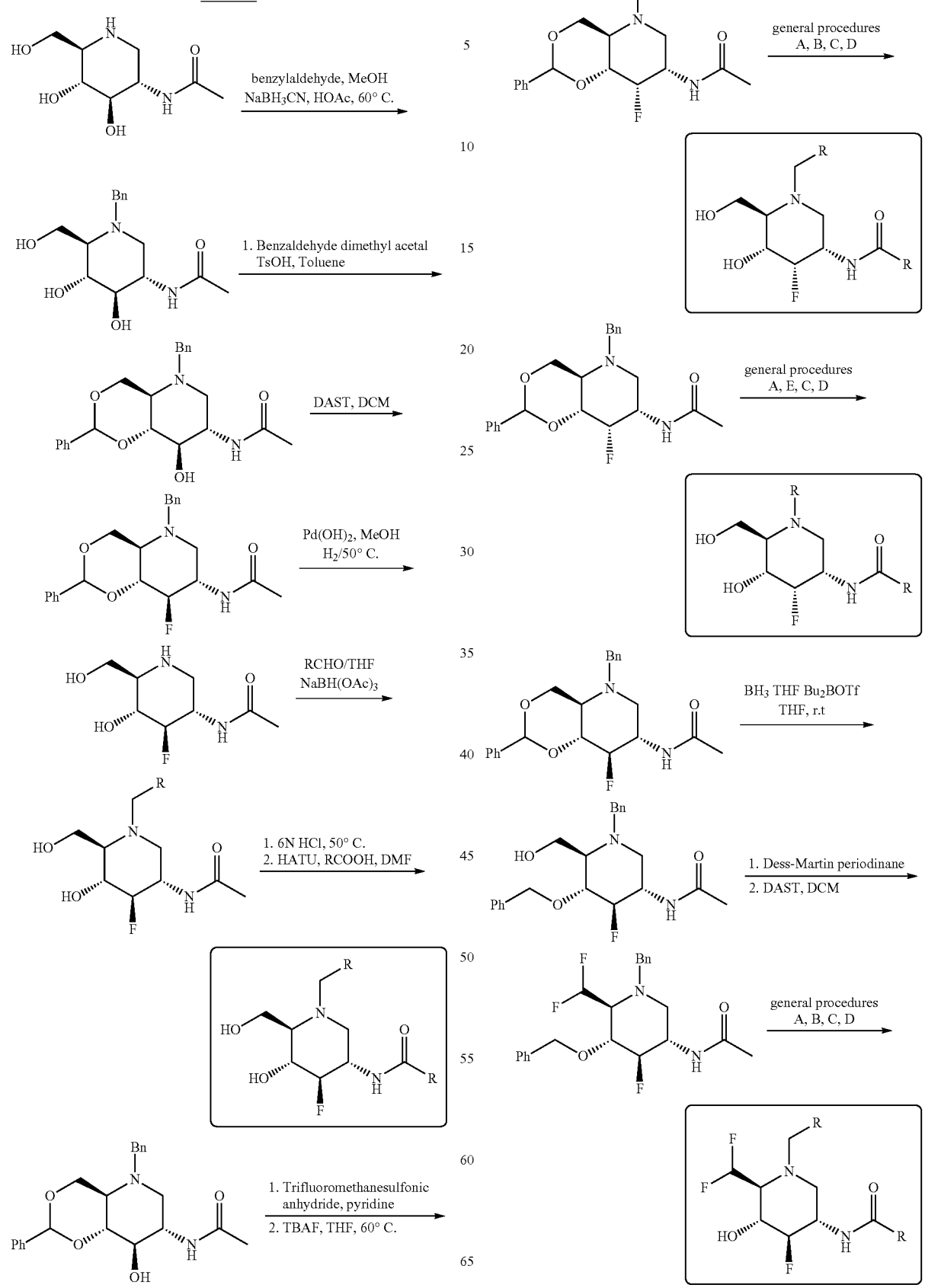

-continued
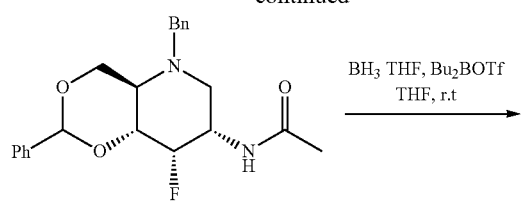
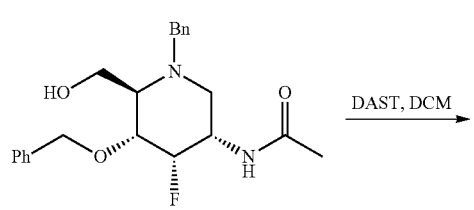
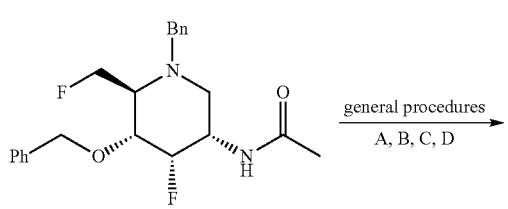
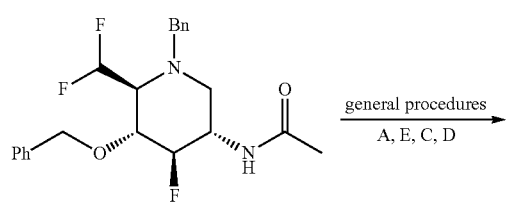
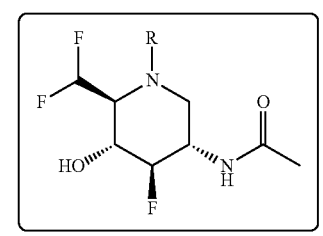
Scheme 3
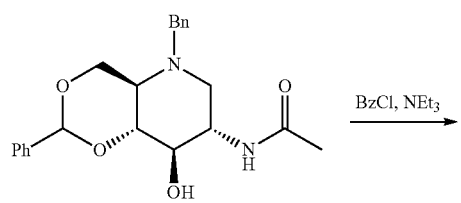
-continued
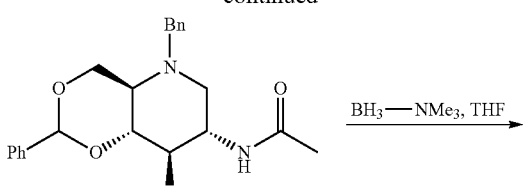
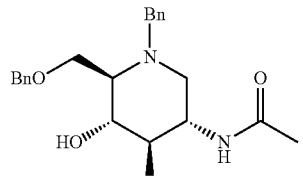
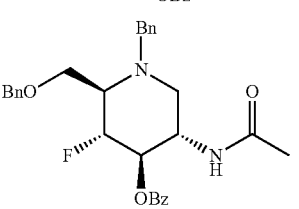
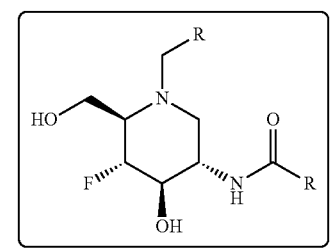
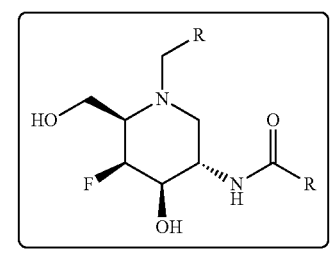

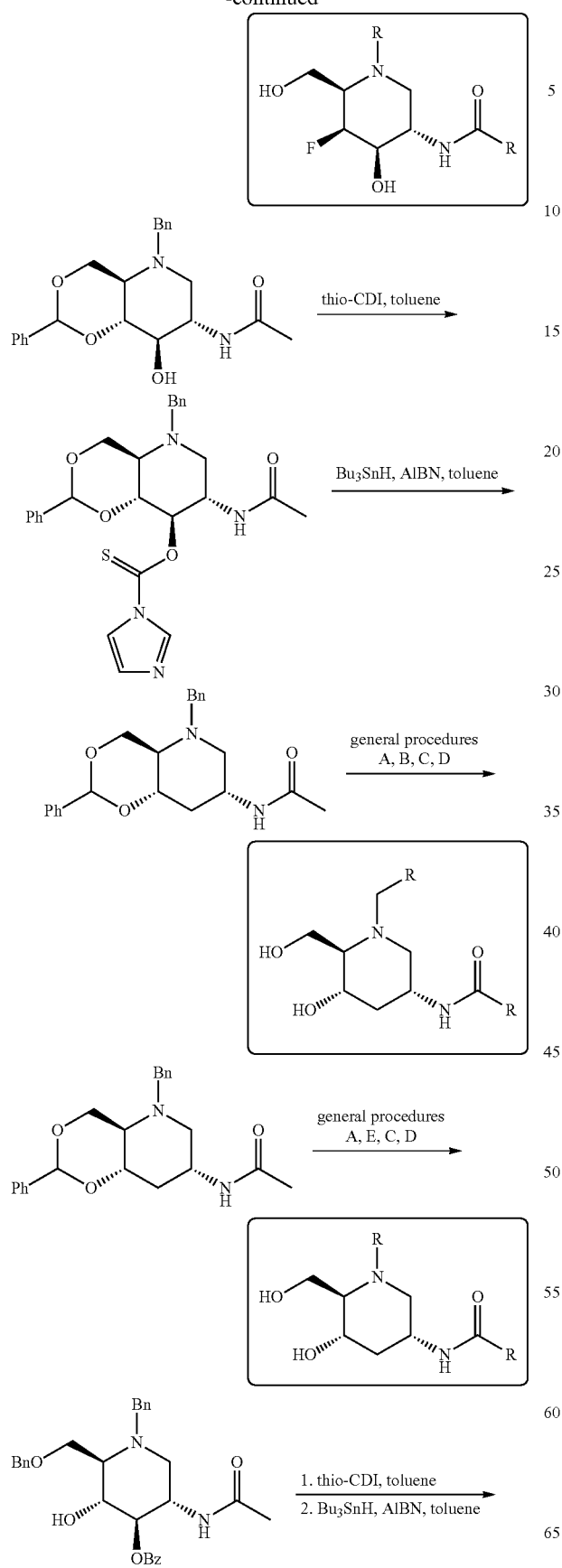
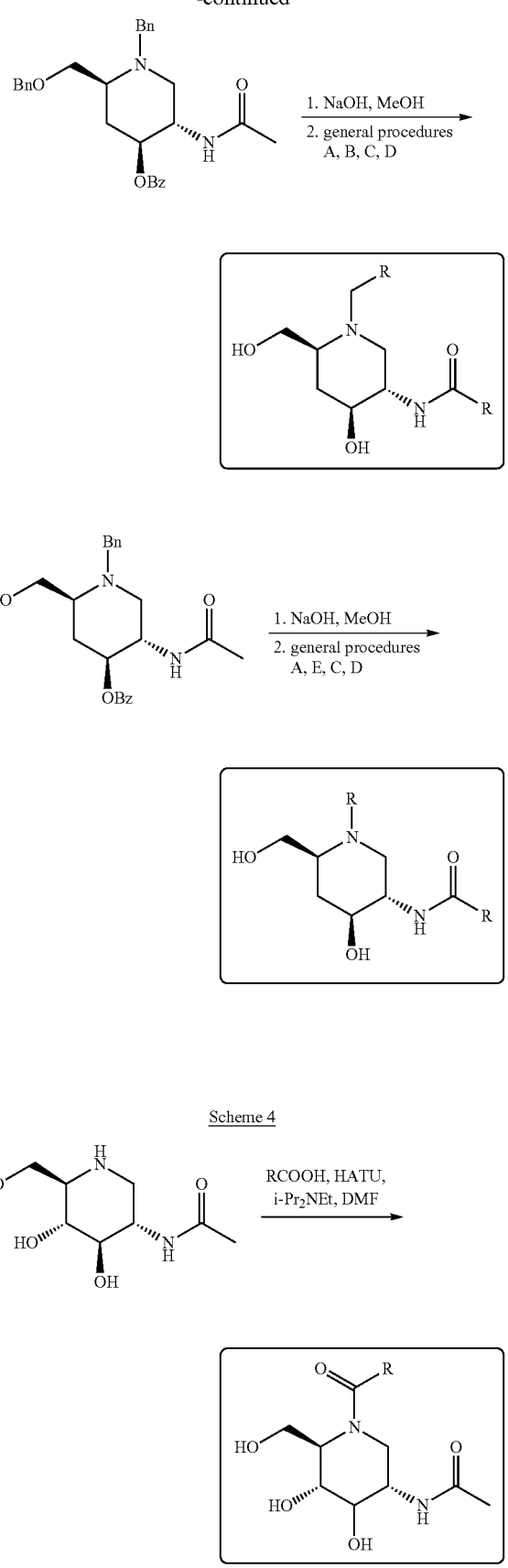
Scheme 4

Scheme 5
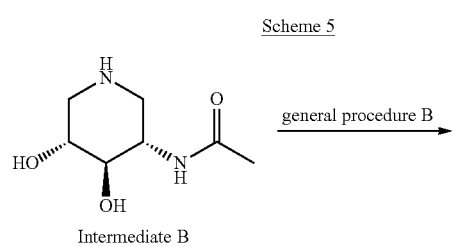
Intermediate B
general procedure B →
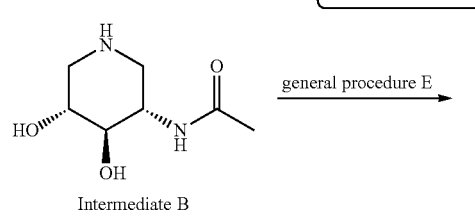
Intermediate B
general procedure E →
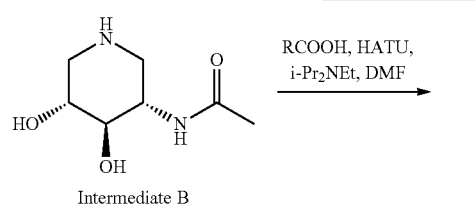
Intermediate B
RCOOH, HATU,
i-Pr₂NEt, DMF →
Scheme 6
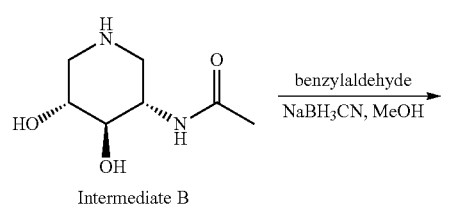
Intermediate B
benzylaldehyde
NaBH₃CN, MeOH →
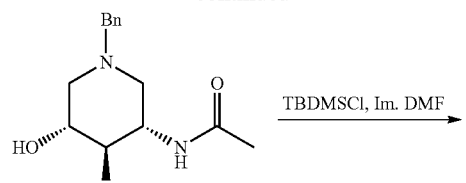
TBDMSCl, Im. DMF →
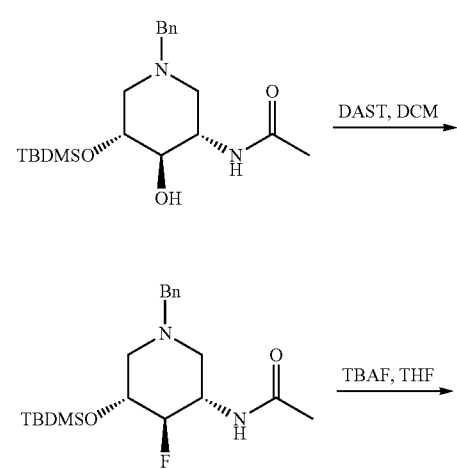
DAST, DCM →
TBAF, THF →
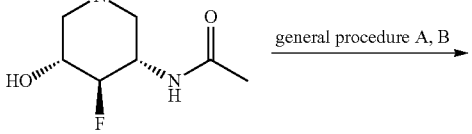
general procedure A, B →
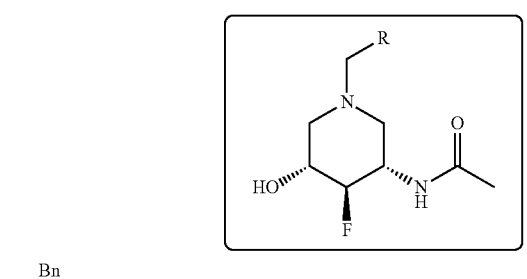
general procedure A, E →
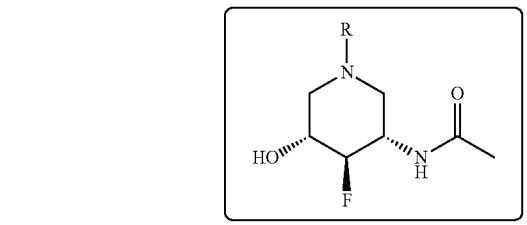

Scheme 7
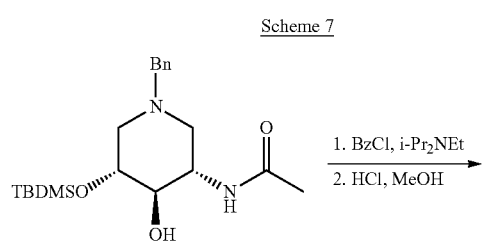
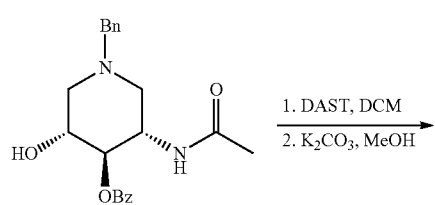
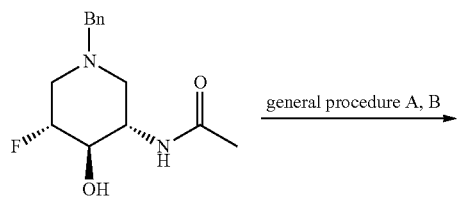
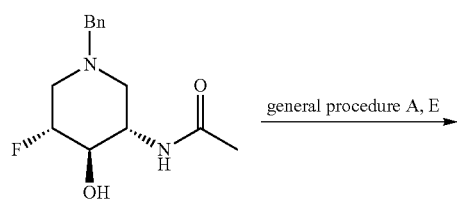
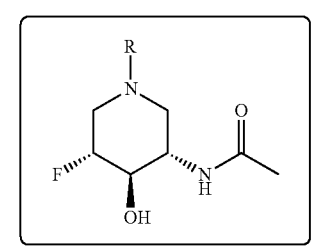
Scheme 8
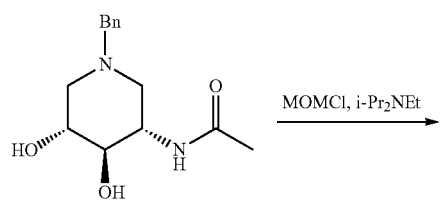
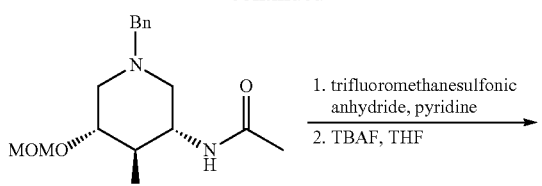
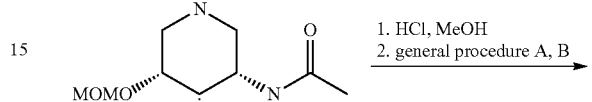
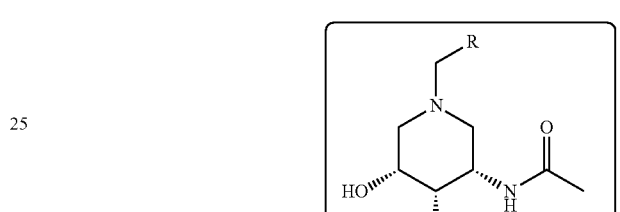
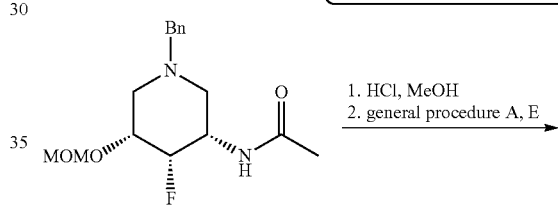
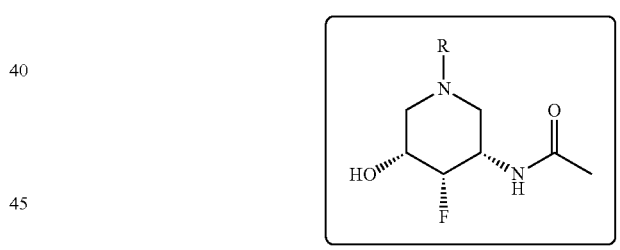
Scheme 9
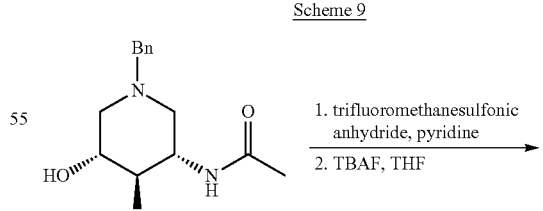
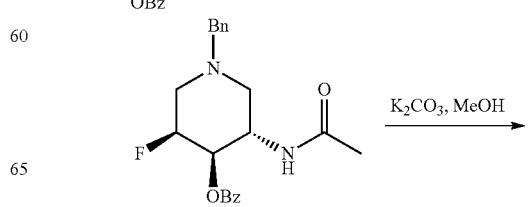

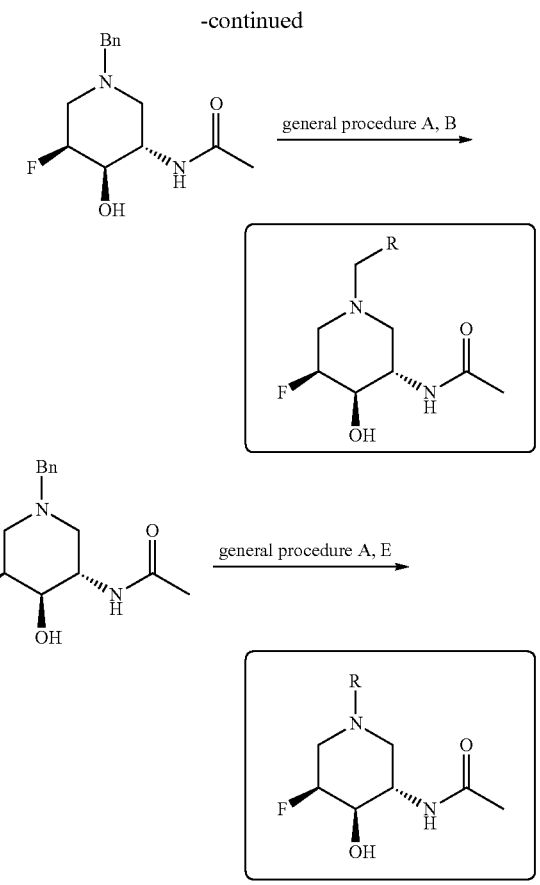

general procedure A, B general procedure A, E

EXAMPLES

Example 1

N-((3S,4R,5R,6R)-4,5-dihydroxy-6-(hydroxymethyl)-1-(4-phenylbutyl)piperidin-3-yl)acetamide

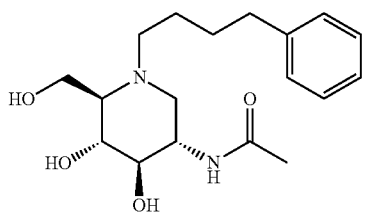 [SMILES: CC(=O)N[C@H]1CN(CCCCc2ccccc2)[C@H](CO)[C@@H](O)[C@@H]1O]

To a solution of N-((3R,4R,5S,6R)-2,4,5-trihydroxy-6-(hydroxymethyl)-tetrahydro-2H-pyran-3-yl)acetamide (N-Acetyl-D-glucosamine) (10 g, 45 mmol) in DMF (150 mL) was added barium oxide (68.8 g, 450 mmol), barium hydroxide (38.5 g, 225 mmol). The resulted mixture was stirred for 10 min followed by the addition of (bromomethyl) benzene (59.8 g, 350 mmol) at 0° C. slowly. After additional 18 hours at room temperature, the solid was filtered out. The filtrate was diluted with water (200 mL) and extracted with dichloromethane (3×200 mL). The combined organic layer was washed with brine (3×100 mL), dried over anhydrous magnesium sulfate and concentrated under concentrated under reduced pressure. The crude residue was purified by re-crystallization (methanol:ethyl acetate 1:2, v/v) to afford N-((3R,4R,5S,6R)-2,4,5-tris(benzyloxy)-6-(benzyloxymethyl)-tetrahydro-2H-pyran-3-yl)acetamide (8.9 g, 34%) as a white solid; (ES, m/z) [M+H]$^+$ 582.2; $^1$H NMR (300 MHz, CDCl$_3$) δ 7.43-7.19 (m, 20H), 5.41 (d, J=8.4 Hz, 1H), 5.23 (br, 1H), 4.89-4.82 (m, 3H), 4.68-4.53 (m, 5H), 4.16-4.14 (m, 1H), 4.08-4.05 (m, 1H), 3.84-3.77 (m, 1H), 3.70-3.63 (m, 2H), 3.33-3.29 (m, 1H), 1.84 (s, 3H).

To a solution of the above material (8.7 g, 15 mmol) in methanol (100 mL) was added anhydrous Pd/C (Palladium 10% on Carbon) (3.6 g) in portions under nitrogen atmosphere. HCOONH$_4$ (2.84 g, 45 mmol) was added slowly while the mixture was maintained at reflux. After additional 1 hour at reflux, the reaction mixture was cooled and the solid was filtered out. The filtrate was concentrated under reduced pressure. The crude residue was washed with ether (3×50 mL) to afford N-((3R,4R,5S,6R)-4,5-bis(benzyloxy)-6-(benzyloxymethyl)-2-hydroxy-tetrahydro-2H-pyran-3-yl)acetamide (4.2 g, 57%) as a white solid; (ES, m/z) [M+H]$^+$ 492.2; $^1$HNMR (300 MHz, CDCl$_3$) $^1$H NMR (300 MHz, CDCl$_3$) δ 7.47-7.21 (m, 15H), 5.18 (d, J=5.6 Hz, 1H), 4.71-4.58 (m, 6H), 4.21-4.17 (m, 1H), 4.13-4.09 (m, 1H), 3.85-3.78 (m, 1H), 3.76-3.67 (m, 2H), 3.43-3.39 (m, 1H), 1.91 (s, 3H).

A solution of the above material (3.4 g, 7 mmol) in ethanol (15 mL) and THF (35 mL) was treated with NaBH$_4$ (1.06 g, 28 mmol) for 12 hours at room temperature. Volatiles were distilled out to give a residue, which was dissolved in dichloromethane (100 mL). The organic layer was washed with brine (2×50 mL), dried over anhydrous magnesium sulfate and concentrated under reduced pressure. The crude residue was purified by a silica gel column, eluted with 1%~4% methanol in dichloromethane to afford N-((2S,3R,4R,5R)-3,4,6-tris(benzyloxy)-1,5-dihydroxy-hexan-2-yl)acetamide (2.9 g, 84%) as colorless oil; (ES, m/z) [M+H]$^+$ 494.2; $^1$H NMR (300 MHz, CDCl$_3$) δ 7.40-7.25 (m, 15H), 6.24 (J=7.8 Hz, 1H, NH), 4.82-4.78 (m, 1H), 4.68-4.60 (m, 6H), 4.28-4.21 (m, 1H), 4.01-3.95 (m, 1H), 3.71-3.62 (m, 4H), 3.52-3.49 (m, 1H), 1.91 (s, 3H).

A solution of DMSO (2.4 g, 31 mmol) in dichloromethane (30 mL) was treated with TFAA (4.8 g, 23 mmol) for 30 min at −78° C. A solution of the above material (2.5 g, 5 mmol) in dichloromethane (25 mL) was added slowly at −78° C. After additional 2 hours at −60° C., the reaction was quenched by triethylamine (10 mL) at −78° C., stirred for 30 min and allowed to warm to room temperature. The mixture was diluted with water (30 mL) and extracted with dichloromethane (3×20 mL). The combined organic layer was washed with brine (2×20 mL), dried over anhydrous magnesium sulfate and concentrated under reduced pressure to afford crude N-((2R,3R,4S)-3,4,6-tris(benzyloxy)-1,5-dioxohexan-2-yl)acetamide as yellow oil, which was used in next step without further purification; (ES, m/z) [M+H]$^+$ 490.1.

To a solution of crude above material, 4-phenylbutan-1-amine (895 mg, 6 mmol) in methanol (20 mL) was added sodium cyanoborohydride (756 mg, 12 mmol) and 4 Å molecule sieve. After stirring for 12 hours at room temperature, the reaction was quenched by water (20 mL), extracted with dichloromethane (3×30 mL). The combined organic layer was washed with brine (2×20 mL), dried over anhydrous magnesium sulfate and concentrated under reduced pressure to give a residue, which was purified by a silica gel column, eluted with 1%~3% methanol in dichloromethane to afford N-((3S,4R,5R,6R)-4,5-bis(benzyloxy)-6-(benzyloxymethyl)-1-(4-phenylbutyl)piperidin-3-yl)acetamide (620 mg, 20% of 2 steps) as a yellow solid. (ES, m/z)

[M+H]+ 607.2; ¹H NMR (300 MHz, CDCl$_3$) δ 7.40-7.21 (m, 20H), 6.23 (br, 1H), 4.64-4.48 (m, 6H), 4.14-4.12 (m, 1H), 3.80-3.76 (m, 2H), 3.73-3.67 (m, 2H), 3.51-3.46 (m, 1H), 3.04-2.97 (m, 2H), 2.62-2.57 (m, 4H), 1.78 (s, 3H), 1.62-1.57 (m, 4H).

To a solution of the above material (304 mg, 0.5 mmol) in methanol (20 mL) was added Pd/C (Palladium 5% on Carbon) (55 mg) under nitrogen atmosphere. The resulting mixture was stirred for 48 hours at 50° C. under hydrogen atmosphere (1 atm). The solids were filtered out, and the filtrate was concentrated under vacuum reduced pressure. The crude residue was purified by Prep-HPLC with the following conditions (Agilent 1200 prep HPLC): Column, X-Bridge C18; mobile phase, water with 0.05% NH$_4$OH and CH$_3$CN (33% up to 45% in 12 min); Detector, 220 nm, to give N-((3S,4R,5R,6R)-4,5-dihydroxy-6-(hydroxymethyl)-1-(4-phenylbutyl)piperidin-3-yl)acetamide (61 mg, 37%) as a white solid; (ES, m/z) [M+H]+ 337.2; ¹H NMR (300 MHz, D$_2$O) δ 7.26-7.13 (m, 5H), 3.96-3.91 (m, 2H), 3.81-3.79 (m, 1H), 3.69-3.59 (m, 1H), 3.57-3.54 (m, 1H), 3.47-3.28 (m, 2H), 3.01-2.85 (m, 3H), 2.60-2.50 (m, 2H), 1.91 (s, 3H), 1.62-1.52 (m, 4H).

The following examples are synthesized according to procedures analogous to the schemes and examples outlined herein.

TABLE 3

| Example | Name | Structure |
|---|---|---|
| 2 | N-((3S,4R,5R)-1-hexyl-4,5-dihydroxypiperidin-3-yl)acetamide | 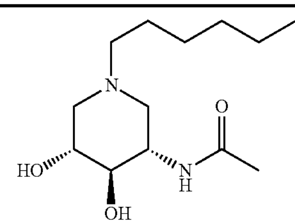 |
| 3 | N-((3S,4R,5R,6R)-4,5-dihydroxy-6-(hydroxymethyl)-1-phenethylpiperidin-3-yl)propionamide | 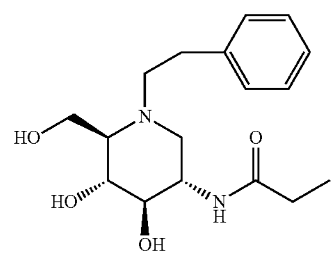 [SMILES: CCC(=O)N[C@H]1CN(CCc2ccccc2)[C@H](CO)[C@@H](O)[C@@H]1O] |
| 4 | N-((3S,4R,5R,6S)-6-(fluoromethyl)-4,5-dihydroxy-1-phenethylpiperidin-3-yl)propionamide | 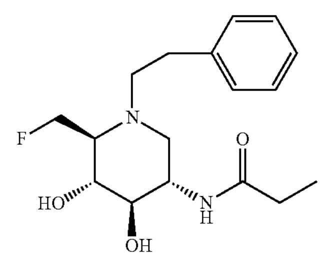 [SMILES: CCC(=O)N[C@H]1CN(CCc2ccccc2)[C@H](CF)[C@@H](O)[C@@H]1O] |
| 5 | N-((3S,4R,5R,6R)-4-fluoro-5-hydroxy-6-(hydroxymethyl)-1-phenethylpiperidin-3-yl)propionamide | 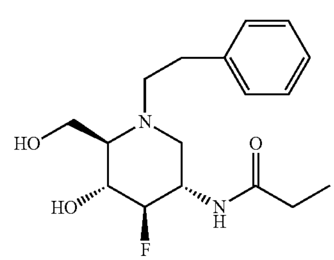 [SMILES: CCC(=O)N[C@H]1CN(CCc2ccccc2)[C@H](CO)[C@@H](O)[C@@H]1F] |
| 6 | N-((3S,4R,5R,6S)-6-(difluoromethyl)-4,5-dihydroxy-1-phenethylpiperidin-3-yl)propionamide | 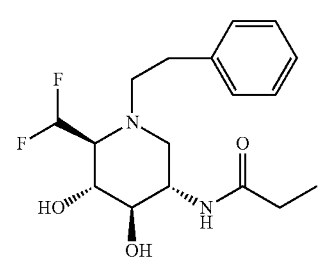 [SMILES: CCC(=O)N[C@H]1CN(CCc2ccccc2)[C@H](C(F)F)[C@@H](O)[C@@H]1O] |

TABLE 3-continued

| Example | Name | Structure |
|---|---|---|
| 7 | N-((3S,4R,5R,6R)-4,5-dihydroxy-6-(hydroxymethyl)-1-(3-phenylpropyl)piperidin-3-yl)propionamide | 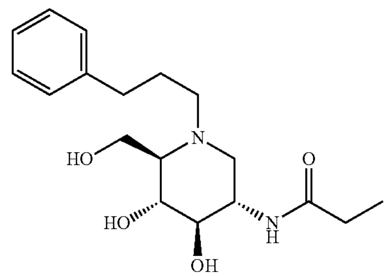 [SMILES: CCC(=O)N[C@H]1CN(CCCc2ccccc2)[C@H](CO)[C@@H](O)[C@@H]1O] |
| 8 | N-((3S,4R,5R,6R)-4-fluoro-5-hydroxy-6-(hydroxymethyl)-1-(3-phenylpropyl)piperidin-3-yl)propionamide | 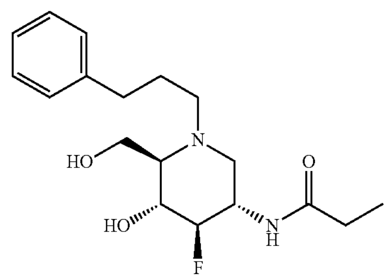 [SMILES: CCC(=O)N[C@H]1CN(CCCc2ccccc2)[C@H](CO)[C@@H](O)[C@@H]1F] |
| 9 | N-((3S,4R,5R,6R)-5-fluoro-4-hydroxy-6-(hydroxymethyl)-1-(3-phenylpropyl)piperidin-3-yl)propionamide | 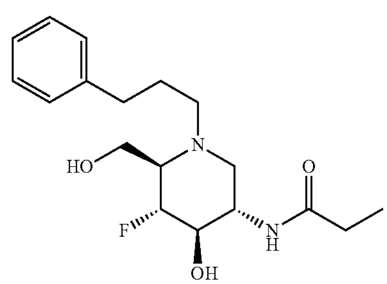 [SMILES: CCC(=O)N[C@H]1CN(CCCc2ccccc2)[C@H](CO)[C@@H](F)[C@@H]1O] |
| 10 | N-((3S,4R,5R,6S)-6-(fluoromethyl)-4,5-dihydroxy-1-(3-phenylpropyl)piperidin-3-yl)propionamide | 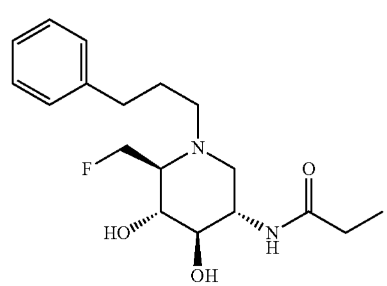 [SMILES: CCC(=O)N[C@H]1CN(CCCc2ccccc2)[C@H](CF)[C@@H](O)[C@@H]1O] |
| 11 | N-((3S,4S,5R,6R)-4-fluoro-5-hydroxy-6-(hydroxymethyl)-1-(3-phenylpropyl)piperidin-3-yl)propionamide | 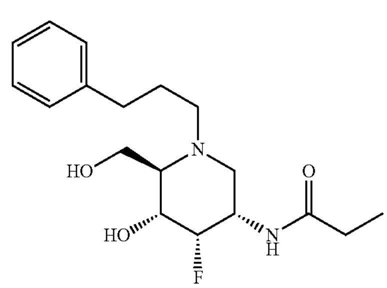 [SMILES: CCC(=O)N[C@H]1CN(CCCc2ccccc2)[C@H](CO)[C@@H](O)[C@H]1F] |

TABLE 3-continued

| Example | Name | Structure |
|---|---|---|
| 12 | N-((3S,4R,5S,6R)-5-fluoro-4-hydroxy-6-(hydroxymethyl)-1-(3-phenylpropyl)piperidin-3-yl)propionamide | 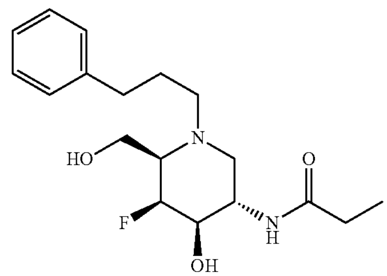 [SMILES: CCC(=O)N[C@H]1CN(CCCc2ccccc2)[C@H](CO)[C@H](F)[C@@H]1O] |
| 13 | N-((3S,4R,5R,6S)-6-(difluoromethyl)-4,5-dihydroxy-1-(3-phenylpropyl)piperidin-3-yl)propionamide | 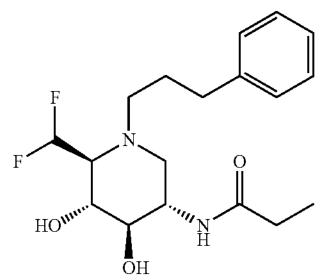 [SMILES: CCC(=O)N[C@H]1CN(CCCc2ccccc2)[C@H](C(F)F)[C@@H](O)[C@@H]1O] |
| 14 | N-((3S,4R,5R,6S)-6-(difluoromethyl)-4-fluoro-5-hydroxy-1-(3-phenylpropyl)piperidin-3-yl)propionamide | 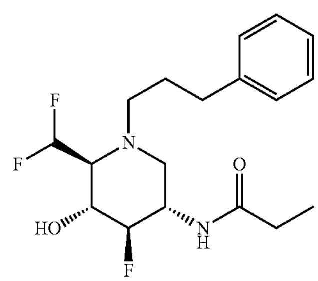 [SMILES: CCC(=O)N[C@H]1CN(CCCc2ccccc2)[C@H](C(F)F)[C@@H](O)[C@@H]1F] |
| 15 | N-((3S,4S,5R,6S)-6-(difluoromethyl)-4-fluoro-5-hydroxy-1-(3-phenylpropyl)piperidin-3-yl)propionamide | 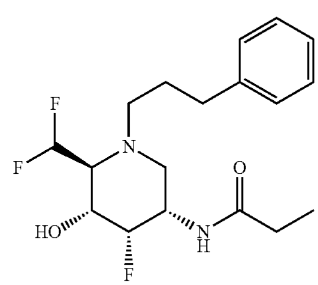 [SMILES: CCC(=O)N[C@H]1CN(CCCc2ccccc2)[C@H](C(F)F)[C@@H](O)[C@H]1F] |
| 16 | N-((3R,5S,6R)-5-hydroxy-6-(hydroxymethyl)-1-(3-phenylpropyl)piperidin-3-yl)propionamide | 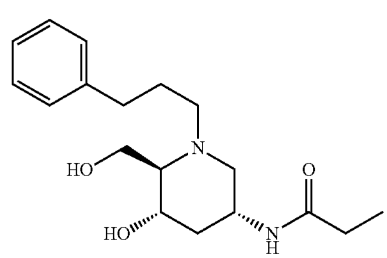 [SMILES: CCC(=O)N[C@@H]1C[C@H](O)[C@@H](CO)N(CCCc2ccccc2)C1] |

TABLE 3-continued

| Example | Name | Structure |
|---|---|---|
| 17 | N-((3S,4S,6S)-4-hydroxy-6-(hydroxymethyl)-1-(3-phenylpropyl)piperidin-3-yl)propionamide | 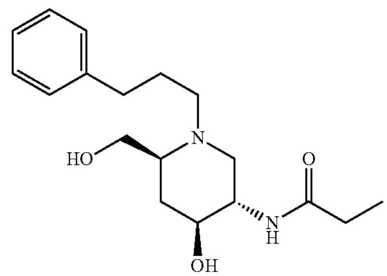 [SMILES: CCC(=O)N[C@H]1CN(CCCc2ccccc2)[C@H](CO)C[C@@H]1O] |
| 18 | N-((3S,4R,5R,6R)-4,5-dihydroxy-6-methyl-1-(3-phenylpropyl)piperidin-3-yl)propionamide | 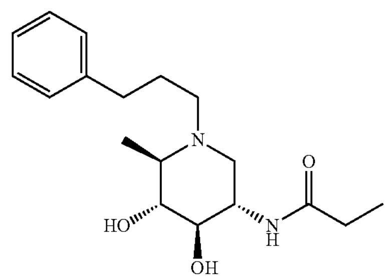 [SMILES: CCC(=O)N[C@H]1CN(CCCc2ccccc2)[C@H](C)[C@@H](O)[C@@H]1O] |
| 19 | N-((3S,4R,5R)-4,5-dihydroxy-1-(3-phenylpropyl)piperidin-3-yl)propionamide | 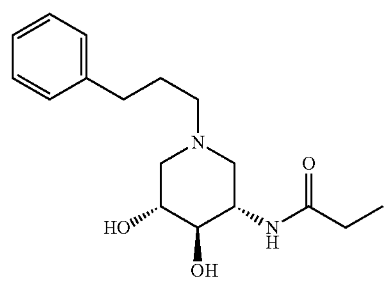 [SMILES: CCC(=O)N[C@H]1CN(CCCc2ccccc2)C[C@@H](O)[C@@H]1O] |
| 20 | N-((3S,4R,5R)-4-fluoro-5-hydroxy-1-(3-phenylpropyl)piperidin-3-yl)propionamide | 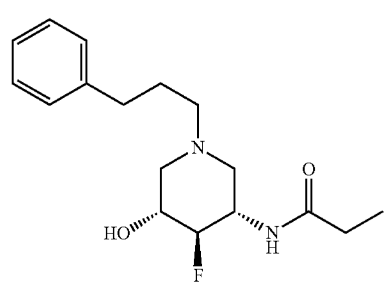 [SMILES: CCC(=O)N[C@H]1CN(CCCc2ccccc2)C[C@@H](O)[C@@H]1F] |
| 21 | N-((3S,4R,5R,6R)-4,5-dihydroxy-6-(hydroxymethyl)-1-(3-phenylpropanoyl)piperidin-3-yl)propionamide | 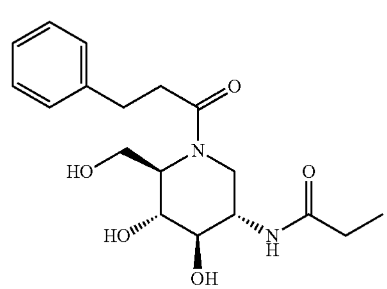 [SMILES: CCC(=O)N[C@H]1CN(C(=O)CCc2ccccc2)[C@H](CO)[C@@H](O)[C@@H]1O] |

TABLE 3-continued

| Example | Name | Structure |
|---|---|---|
| 22 | N-((3S,4R,5R,6R)-1-(3-(6-fluoropyridin-3-yl)propyl)-4,5-dihydroxy-6-(hydroxymethyl)piperidin-3-yl)propionamide | 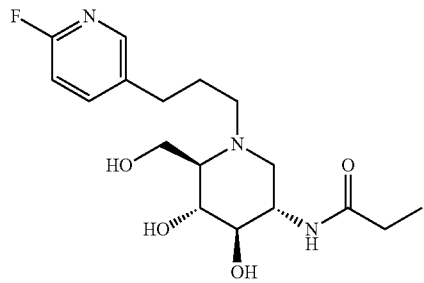 [SMILES: CCC(=O)N[C@H]1CN(CCCc2ccc(F)nc2)[C@H](CO)[C@@H](O)[C@@H]1O] |
| 23 | N-((3S,4R,5R,6R)-4,5-dihydroxy-6-(hydroxymethyl)-1-(4,4,4-trifluorobutyl)piperidin-3-yl)propionamide | 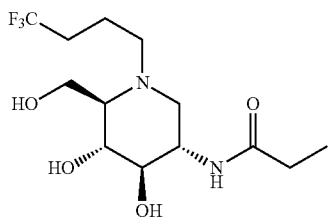 [SMILES: CCC(=O)N[C@H]1CN(CCCC(F)(F)F)[C@H](CO)[C@@H](O)[C@@H]1O] |
| 24 | N-((3S,4R,5R,6R)-4,5-dihydroxy-6-(hydroxymethyl)-1-(3-(5-(trifluoromethoxy)benzo[d]thiazol-2-yl)propyl)piperidin-3-yl)propionamide | 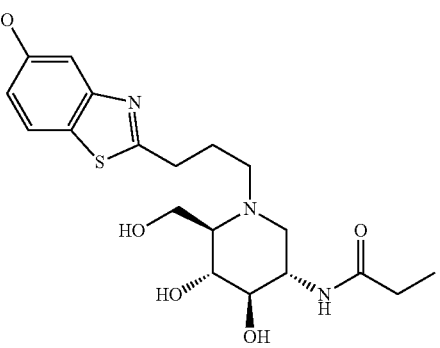 |
| 25 | N-((3S,4R,5R,6R)-4,5-dihydroxy-6-(hydroxymethyl)-1-((Z)-5,5,5-trifluoropent-3-en-1-yl)piperidin-3-yl)propionamide | 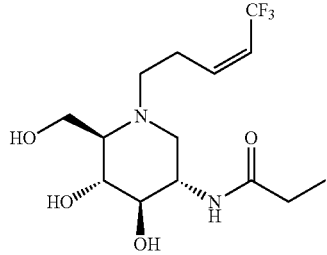 [SMILES: CCC(=O)N[C@H]1CN(CC/C=C\C(F)(F)F)[C@H](CO)[C@@H](O)[C@@H]1O] |
| 26 | N-((3S,4R,5R,6R)-4,5-dihydroxy-6-(hydroxymethyl)-1-(pent-4-yn-1-yl)piperidin-3-yl)propionamide | 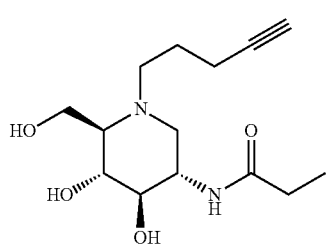 [SMILES: C#CCCCN1C[C@H](NC(=O)CC)[C@@H](O)[C@H](O)[C@H]1CO] |
| 27 | N-((3S,4R,5R,6R)-1-butyryl-4,5-dihydroxy-6-(hydroxymethyl)piperidin-3-yl)propionamide | 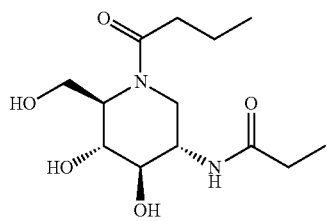 |

TABLE 3-continued

| Example | Name | Structure |
|---|---|---|
| 28 | N-((3S,4R,5R,6R)-1-(3-(6-fluoropyridin-3-yl)propanoyl)-4,5-dihydroxy-6-(hydroxymethyl)piperidin-3-yl)propionamide | 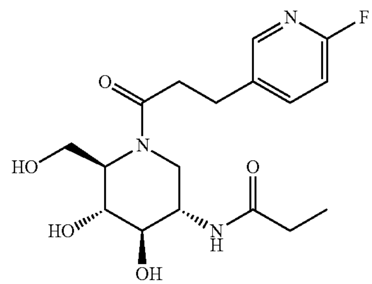 [SMILES: CCC(=O)N[C@H]1CN(C(=O)CCc2ccc(F)nc2)[C@H](CO)[C@@H](O)[C@@H]1O] |
| 29 | N-((3S,4R,5R,6R)-1-cinnamyl-4,5-dihydroxy-6-(hydroxymethyl)piperidin-3-yl)propionamide | 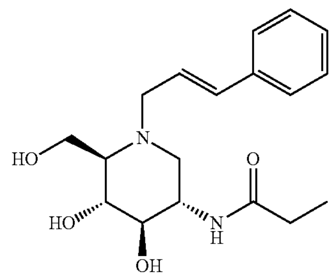 [SMILES: CCC(=O)N[C@H]1CN(C/C=C/c2ccccc2)[C@H](CO)[C@@H](O)[C@@H]1O] |
| 30 | N-((3S,4R,5R,6R)-4,5-dihydroxy-6-(hydroxymethyl)-1-(3-phenylprop-2-yn-1-yl)piperidin-3-yl)propionamide | 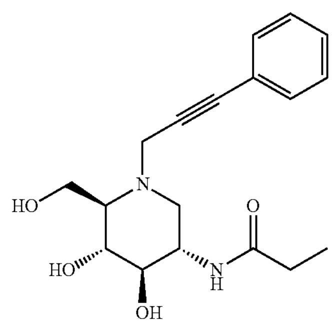 [SMILES: CCC(=O)N[C@H]1CN(CC#Cc2ccccc2)[C@H](CO)[C@@H](O)[C@@H]1O] |
| 31 | N-((3S,4R,5R,6R)-1-((E)-3-(6-fluoropyridin-3-yl)allyl)-4,5-dihydroxy-6-(hydroxymethyl)piperidin-3-yl)propionamide | 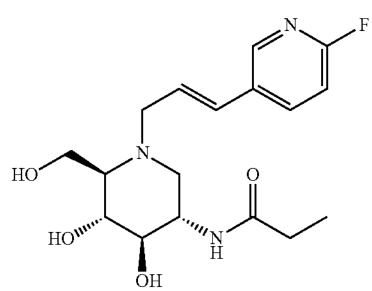 [SMILES: CCC(=O)N[C@H]1CN(C/C=C/c2ccc(F)nc2)[C@H](CO)[C@@H](O)[C@@H]1O] |
| 32 | N-((3S,4R,5R,6R)-1-(3-(6-fluoropyridin-3-yl)prop-2-yn-1-yl)-4,5-dihydroxy-6-(hydroxymethyl)piperidin-3-yl)propionamide | 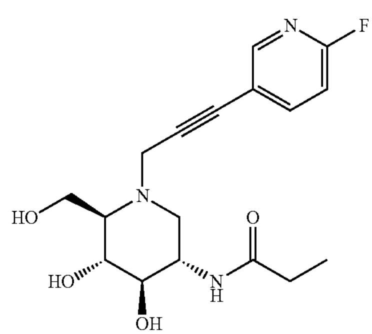 [SMILES: CCC(=O)N[C@H]1CN(CC#Cc2ccc(F)nc2)[C@H](CO)[C@@H](O)[C@@H]1O] |

Biological Activity

Assay for Determination of $K_I$ Values for Inhibition of O-GlcNAcase Activity Experimental Procedure for Kinetic Analyses:

Enzymatic reactions were carried out in a reaction containing 50 mM NaH$_2$PO$_4$, 100 mM NaCl and 0.1% BSA (pH 7.0) using 2 mM 4-Methylumbelliferyl N-acetyl-β-D-glucosaminide dihydrate (Sigma M2133) dissolved in ddH$_2$O, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_I$ values were determined using the Cheng-Prusoff equation; the $K_m$ of O-GlcNAcase for substrate was 0.2 mM.

Many compounds of the invention exhibit $K_I$ values for inhibition of O-GlcNAcase in the range 0.1 nM-50 µM.

Assay for Determination of $K_T$ Values for Inhibition of β-Hexosaminidase Activity Experimental Procedure for Kinetic Analyses:

Enzymatic reactions were carried out in a reaction containing 50 mM NaH$_2$PO$_4$, 100 mM NaCl and 0.1% BSA (pH 7.0) using 2 mM 4-Methylumbelliferyl N-acetyl-β-D-glucosaminide dihydrate (Sigma M2133) dissolved in ddH$_2$O, as a substrate. The amount of purified human β-hexosaminidase enzyme used in the reaction was 24 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

$K_I$ values were determined using the Cheng-Prusoff equation.

When tested in this assay, many of the compounds described herein exhibit $K_I$ values for inhibition of β-hexosaminidase in the range 10 nM to greater than 100 uM.

The selectivity ratio for inhibition of O-GlcNAcase over β-hexosaminidase is defined here as:

$$K_I(\beta\text{-hexosaminidase})/K_I(\text{O-GlcNAcase})$$

In general, many of the compounds described herein exhibit a selectivity ratio in the range of about 10 to 100000. Thus, many compounds of the invention exhibit high selectivity for inhibition of O-GlcNAcase over β-hexosaminidase.

Assay for Determination of Cellular Activity for Compounds that Inhibit O-GlcNAcase Activity Inhibition of O-GlcNAcase, which removes O-GlcNAc from cellular proteins, results in an increase in the level of O-GlcNAcylated protein in cells. An increase in O-GlcNAcylated protein can be measured by an antibody, such as RL-2, that binds to O-GlcNAcylated protein. The amount of O-GlcNAcylated protein:RL2 antibody interaction can be measured by enzyme linked immunosorbant assay (ELISA) procedures.

A variety of tissue culture cell lines, expressing endogenous levels of O-GlcNAcase, can be utilized; examples include rat PC-12, and human U-87, or SK-N-SH cells. In this assay, rat PC-12 cells are plated in 96-well plates with approximately 10,000 cells/well. Compounds to be tested are dissolved in DMSO, either 2 or 10 mM stock solution, and then diluted with DMSO and water in a two-step process using a Tecan workstation. Cells are treated with diluted compounds for 24 h (5.4 µL into 200 41 well volume) to reach a final concentration of inhibitor desired to measure a compound concentration dependent response, typically, ten 3 fold dilution steps, starting at 10 µM are used to determine a concentration response curve. To prepare a cell lysate, the media from compound treated cells is removed, the cells are washed once with phosphate buffered saline (PBS) and then lysed for 5 minutes at room temperature in 50 µL, of Phosphosafe reagent (Novagen Inc, Madison, Wis.) with protease inhibitors and PMSF. The cell lysate is collected and transferred to a new plate, which is then either coated to assay plates directly or frozen −80° C. until used in the ELISA procedure. If desired, the total protein concentration of samples is determined using 20 µL, of the sample using the BCA method.

The ELISA portion of the assay is performed in a black Maxisorp 96-well plate that is coated overnight at 4° C. with 100 µL/well of the cell lysate (1:10 dilution of the lysate with PBS containing protease inhibitors, phosphatase inhibitors, and PMSF). The following day the wells are washed 3 times with 300 µL/well of Wash buffer (Tris-buffered saline with 0.1% Tween 20). The wells are blocked with 100 µL/well Blocking buffer (Tris buffered saline w/0.05% Tween 20 and 2.5% Bovine serum albumin). Each well is then washed two times with 300 µL/well of wash buffer. The anti O-GlcNAc antibody RL-2 (Abcam, Cambridge, Mass.), diluted 1:1000 in blocking buffer, is added at 100 µL/well. The plate is sealed and incubated at 37° C. for 2 h with gentle shaking. The wells are then washed 3-times with 300 µL/well wash buffer. To detect the amount of RL-2 bound horse-radish peroxidase (HRP) conjugated goat anti-mouse secondary antibody (diluted 1:3000 in blocking buffer) is added at 100 µL/well. The plate is incubated for 60 min at 37° C. with gentle shaking. Each well is then washed 3-times with 300 µL/well wash buffer. The detection reagent is added, 100 µL/well of Amplex Ultra RED reagent (prepared by adding 30 µL of 10 mM Amplex Ultra Red stock solution to 10 mL PBS with 18 µL 3% hydrogen peroxide, H$_2$O$_2$). The detection reaction is incubated for 15 minutes at room temperature and then read with excitation at 530 nm and emission at 590 nm.

The amount of O-GlcNAcylated protein, as detected by the ELISA assay, is plotted for each concentration of test compound using standard curve fitting algorithms for sigmoidal dose response curves. The values for a four parameter logistic curve fit of the data are determined, with the inflection point of the curve being the potency value for the test compound.

Assay for Determination of Apparent Permeability ($P_{app}$)

Bi-directional transport is evaluated in LLC-PK1 cells in order to determine apparent permeability ($P_{app}$). LLC-PK1 cells can form a tight monolayer and therefore can be used to assess vectorial transport of compounds from basolateral to apical (B→A) and from apical to basolateral (A→B).

To determine $P_{app}$, LLC-PK1 cells are cultured in 96-well transwell culture plates (Millipore). Solutions containing the test compounds (1 µM) are prepared in Hank's Balanced Salt Solution with 10 mM HEPES. Substrate solution (150 µL) is added to either the apical (A) or the basolateral (B) compartment of the culture plate, and buffer (150 µL) is added to the compartment opposite to that containing the compound. At t=3 h, 50 µL samples are removed from both sides of monolayers dosed with test compound and placed in 96 well plates, scintillant (200 µL) or internal standard (100 µL labetolol 1 µM) is added to the samples and concentration is determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 µM) is used as the positive control. The experiment is performed in triplicate.

The apparent permeability, $P_{app}$, is calculated by the following formula for samples taken at t=3 h:

$$P_{app} = \frac{\text{Volume of Receptor Chamber (mL)}}{[\text{Area of membrane (cm}^2)]} \times \frac{\Delta \text{ in Concentration (µM)}}{\Delta \text{ in Time}(s)}$$
$$[\text{Initial Concentration (µM)}]$$

Where: Volume of Receptor Chamber is 0.15 mL; Area of membrane is 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). $P_{app}$ is expressed as $10^{-6}$ cm/s. The $P_{app}$ (LLC-PK1 cells) are the average of the $P_{app}$ for transport from A to B and $P_{app}$ for transport from B to A at t=3 h:

$$P_{app}(LLC-PK1\text{ Cells}) = \frac{P_{app}(A \to B) + P_{app}(B \to A)}{2}$$

Representative data from the binding, cell-based, and permeability assays described above are shown in the following table. Certain compounds of the invention exhibit superior potency or permeability in one or more of these assays.

TABLE 4

| Example | Structure | Cell-based ELISA EC$_{50}$ (nM) | Fluorescence-based hOGA Ki (nM) | Papp LLC-PK1 cells ($10^{-6}$ cm/s) |
|---|---|---|---|---|
| 1 | 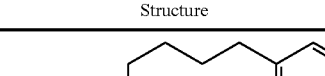 | ND | 2578 | ND |

The present invention has been described with regard to one or more embodiments. However, it will be apparent to persons skilled in the art that a number of variations and modifications can be made without departing from the scope of the invention as defined in the claims.

REFERENCES

1. C. R. Tones, G. W. Hart, *J Biol Chem* 1984, 259, 3308-17.
2. R. S. Haltiwanger, G. D. Holt, and G. W. Hart, *J Biol Chem* 1990, 265, 2563-8.
3. L. K. Kreppel, M. A. Blomberg, and G. W. Hart, *J Biol Chem* 1997, 272, 9308-15.
4. W. A. Lubas, et al., *J Biol Chem* 1997, 272, 9316-24.
5. W. A. Lubas, J. A. Hanover, *J Biol Chem* 2000, 275, 10983-8.
6. D. L. Dong, G. W. Hart, *J Biol Chem* 1994, 269, 19321-30.
7. Y. Gao, et al., *J Biol Chem* 2001, 276, 9838-45.
8. E. P. Roquemore, et al., *Biochemistry* 1996, 35, 3578-86.
9. S. P. Jackson, R. Tjian, *Cell* 1988, 55, 125-33.
10. W. G. Kelly, M. E. Dahmus, and G. W. Hart, *J Biol Chem* 1993, 268, 10416-24.
11. M. D. Roos, et al., *Mol Cell Biol* 1997, 17, 6472-80.
12. N. Lamarre-Vincent, L. C. Hsieh-Wilson, *J Am Chem Soc* 2003, 125, 6612-3.
13. F. Zhang, et al., *Cell* 2003, 115, 715-25.
14. K. Vosseller, et al., *Proc Natl Acad Sci USA* 2002, 99, 5313-8.
15. W. A. Lubas, et al., *Biochemistry* 1995, 34, 1686-94.
16. L. S. Griffith, B. Schmitz, *Biochem Biophys Res Commun* 1995, 213, 424-31.
17. R. N. Cole, G. W. Hart, *J Neurochem* 1999, 73, 418-28.
18. I. Braidman, et al., *Biochem J* 1974, 143, 295-301.
19. R. Ueno, C. S. Yuan, *Biochim Biophys Acta* 1991, 1074, 79-84.
20. C. Toleman, et al., *J Biol Chem* 2004, 279, 53665-73.
21. F. Liu, et al., *Proc Natl Acad Sci USA* 2004, 101, 10804-9.
22. T. Y. Chou, G. W. Hart, *Adv Exp Med Biol* 2001, 491, 413-8.

23. M. Goedert, et al., *Neuron* 1992, 8, 159-68.
24. M. Goedert, et al., *Neuron* 1989, 3, 519-26.
25. E. Kopke, et al., *J Biol Chem* 1993, 268, 24374-84.
26. H. Ksiezak-Reding, W. K. Liu, and S. H. Yen, *Brain Res* 1992, 597, 209-19.
27. P. V. Arriagada, et al., *Neurology* 1992, 42, 631-9.
28. K. P. Riley, D. A. Snowdon, and W. R. Markesbery, *Ann Neurol* 2002, 51, 567-77.
29. I. Alafuzoff, et al., *Acta Neuropathol (Berl)* 1987, 74, 209-25.
30. C. X. Gong, et al., *J Neural Transm* 2005, 112, 813-38.
31. K. Iqbal, et al., *J Neural Transm Suppl* 2002, 309-19.
32. K. Iqbal, et al., *J Mol Neurosci* 2003, 20, 425-9.
33. W. Noble, et al., *Proc Natl Acad Sci USA* 2005, 102, 6990-5.
34. S. Le Corre, et al., *Proc Natl Acad Sci USA* 2006, 103, 9673-8.
35. S. J. Liu, et al., *J Biol Chem* 2004, 279, 50078-88.
36. G. Li, H. Yin, and J. Kuret, *J Biol Chem* 2004, 279, 15938-45.
37. T. Y. Chou, G. W. Hart, and C. V. Dang, *J Biol Chem* 1995, 270, 18961-5.
38. X. Cheng, G. W. Hart, *J Biol Chem* 2001, 276, 10570-5.
39. X. Cheng, et al., *Biochemistry* 2000, 39, 11609-20.
40. L. S. Griffith, B. Schmitz, *Eur J Biochem* 1999, 262, 824-31.
41. K. Kamemura, G. W. Hart, *Prog Nucleic Acid Res Mol Biol* 2003, 73, 107-36.
42. L. Wells, et al., *J Biol Chem* 2004, 279, 38466-70.
43. L. Bertram, et al., *Science* 2000, 290, 2302-3.
44. S. Hoyer, et al., *Journal of Neural Transmission* 1998, 105, 423-438.
45. C. X. Gong, et al., *Journal of Alzheimers Disease* 2006, 9, 1-12.
46. W. J. Jagust, et al., *Journal of Cerebral Blood Flow and Metabolism* 1991, 11, 323-330.
47. S. Hoyer, *Experimental Gerontology* 2000, 35, 1363-1372.
48. S. Hoyer, in *Frontiers in Clinical Neuroscience: Neurodegeneration and Neuroprotection, Vol.* 541, 2004, 135-152.
49. R. N. Kalaria, S. I. Hank, *Journal of Neurochemistry* 1989, 53, 1083-1088.
50. I. A. Simpson, et al., *Annals of Neurology* 1994, 35, 546-551.
51. S. M. de la Monte, J. R. Wands, *Journal of Alzheimers Disease* 2005, 7, 45-61.
52. X. W. Zhu, G. Perry, and M. A. Smith, *Journal of Alzheimers Disease* 2005, 7, 81-84.
53. J. C. de la Torre, *Neurological Research* 2004, 26, 517-524.
54. S. Marshall, W. T. Garvey, and R. R. Traxinger, *Faseb J* 1991, 5, 3031-6.
55. S. P. Iyer, Y. Akimoto, and G. W. Hart, *J Biol Chem* 2003, 278, 5399-409.
56. K. Brickley, et al., *J Biol Chem* 2005, 280, 14723-32.
57. S. Knapp, C. H. Yang, and T. Haimowitz, *Tetrahedron Letters* 2002, 43, 7101-7104.
58. S. P. Iyer, G. W. Hart, *J Biol Chem* 2003, 278, 24608-16.
59. M. Jinek, et al., *Nat Struct Mol Biol* 2004, 11, 1001-7.
60. K. Kamemura, et al., *J Biol Chem* 2002, 277, 19229-35.
61. Y. Deng, et al., *FASEB J.* 2007, fj.07-8309com.
62. L. F. Lau, et al., *Curr Top Med Chem* 2002, 2, 395-415.
63. M. P. Mazanetz, P. M. Fischer, *Nature Reviews Drug Discovery* 2007, 6, 464-479.
64. S. A. Yuzwa, et al., *Nat Chem Biol* 2008, 4, 483-490.
65. P. Bounelis, et al., *Shock* 2004, 21 170 Suppl. 2, 58-58.
66. N. Fulop, et al., *Circulation Research* 2005, 97, E28-E28.
67. J. Liu, R. B. Marchase, and J. C. Chatham, *Faseb Journal* 2006, 20, A317-A317.
68. R. Marchase, et al., PCT Int. Appl. WO 2006016904 2006.
69. N. Fulop, et al., *Journal of Molecular and Cellular Cardiology* 2004, 37, 286-287.
70. N. Fulop, et al., *Faseb Journal* 2005, 19, A689-A690.
71. J. Liu, R. B. Marchase, and J. C. Chatham, *Journal of Molecular and Cellular Cardiology* 2007, 42, 177-185.
72. L. G. Not, et al., *Faseb Journal* 2006, 20, A1471-A1471.
73. S. L. Yang, et al., *Shock* 2006, 25, 600-607.
74. L. Y. Zou, et al., *Faseb Journal* 2005, 19, A1224-A1224.
75. R. B. Marchase, et al., *Circulation* 2004, 110, 1099-1099.
76. J. Liu, et al., *Journal of Molecular and Cellular Cardiology* 2006, 40, 303-312.
77. J. Liu, J. C. Chatham, and R. B. Marchase, *Faseb Journal* 2005, 19, A691-A691.
78. T. Nagy, et al., *American Journal of Physiology-Cell Physiology* 2006, 290, C57-C65.
79. N. Fulop, R. B. Marchase, and J. C. Chatham, *Cardiovascular Research* 2007, 73, 288-297.
80. T. Lefebvre, et al., *Expert Review of Proteomics* 2005, 2, 265-275.
81. B. Henrissat, A. Bairoch, *Biochem J* 1993, 293 (Pt 3), 781-8.
82. B. Henrissat, A. Bairoch, *Biochem J* 1996, 316 (Pt 2), 695-6.
83. L. Wells, K. Vosseller, and G. W. Hart, *Science* 2001, 291, 2376-8.
84. J. A. Hanover, *FASEB J* 2001, 15, 1865-76.
85. D. A. McClain, et al., *Proc Natl Acad Sci USA* 2002, 99, 10695-9.
86. P. J. Yao, P. D. Coleman, *J Neurosci* 1998, 18, 2399-411.
87. W. H. Yang, et al., *Nature Cell Biology* 2006, 8, 1074-U53.
88. B. Triggs-Raine, D. J. Mahuran, and R. A. Gravel, *Adv Genet* 2001, 44, 199-224.
89. D. Zhou, et al., *Science* 2004, 1786-89.
90. G. Legler, et al., *Biochim Biophys Acta* 1991, 1080, 89-95.
91. M. Horsch, et al., *Eur J Biochem* 1991, 197, 815-8.
92. J. Liu, et al., *Chem Biol* 2001, 8, 701-11.
93. S. Knapp, et al., *J. Am. Chem. Soc.* 1996, 118, 6804-6805.
94. V. H. Lillelund, et al., *Chem Rev* 2002, 102, 515-53.
95. R. J. Konrad, et al., *Biochem J* 2001, 356, 31-41.
96. K. Liu, et al., *J Neurochem* 2004, 89, 1044-55.
97. G. Parker, et al., *J Biol Chem* 2004, 279, 20636-42.
98. E. B. Arias, J. Kim, and G. D. Cartee, *Diabetes* 2004, 53, 921-30.
99. A. Junod, et al., *Proc Soc Exp Biol Med* 1967, 126, 201-5.
100. R. A. Bennett, A. E. Pegg, *Cancer Res* 1981, 41, 2786-90.
101. K. D. Kroncke, et al., *Biol Chem Hoppe Seyler* 1995, 376, 179-85.
102. H. Yamamoto, Y. Uchigata, and H. Okamoto, *Nature* 1981, 294, 284-6.
103. K. Yamada, et al., *Diabetes* 1982, 31, 749-53.
104. V. Burkart, et al., *Nat Med* 1999, 5, 314-9.
105. M. D. Roos, et al., *Proc Assoc Am Physicians* 1998, 110, 422-32.
106. Y. Gao, G. J. Parker, and G. W. Hart, *Arch Biochem Biophys* 2000, 383, 296-302.

107. R. Okuyama, M. Yachi, *Biochem Biophys Res Commun* 2001, 287, 366-71.
108. N. E. Zachara, et al., *J Biol Chem* 2004, 279, 30133-42.
109. J. A. Hanover, et al., *Arch Biochem Biophys* 1999, 362, 38-45.
110. K. Liu, et al., *Mol Cell Endocrinol* 2002, 194, 135-46.
111. M. S. Macauley, et al., *J Biol Chem* 2005, 280, 25313-22.
112. B. L. Mark, et al., *J Biol Chem* 2001, 276, 10330-7.
113. R. S. Haltiwanger, K. Grove, and G. A. Philipsberg, *J Biol Chem* 1998, 273, 3611-7.
114. D. J. Miller, X. Gong, and B. D. Shur, *Development* 1993, 118, 1279-89.
115. L. Y. Zou, et al., *Shock* 2007, 27, 402-408.
116. J. B. Huang, A. J. Clark, and H. R. Petty, *Cellular Immunology* 2007, 245, 1-6.
117. N. E. Zachara, et al., Abstract 418 in *Joint Meeting of the Society for Glycobiology and the Japanese Society of Carbohydrate Research*. Honolulu, Hi., 2004.
118. L. Y. Zou, et al., *Faseb Journal* 2006, 20, A1471-A1471.
119. V. Champattanachai, R. B. Marchase, and J. C. Chatham, *American Journal of Physiology-Cell Physiology* 2007, 292, C178-C187.
120. V. Champattanachai, R. B. Marchase, and J. C. Chatham, *American Journal of Physiology-Cell Physiology* 2008, 294, C1509-C1520.
121. I. Khlistunova, et al., *Current Alzheimer Research* 2007, 4, 544-546.
122. P. Friedhoff, et al., *Biochemistry* 1998, 37, 10223-10230.
123. M. Pickhardt, et al., *Journal of Biological Chemistry* 2005, 280, 3628-3635.

What is claimed is:
1. A compound of Formula (I) or a pharmaceutically acceptable salt thereof:

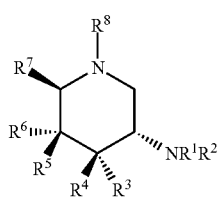

(I)

wherein
$R^1$ is H;
$R^2$ is $C_{1-6}$ acyl;
$R^3$ is H and $R^4$ is OH, or $R^3$ is H and $R^4$ is H, or $R^3$ is H and $R^4$ is F, or $R^3$ is F and $R^4$ is H, or $R^3$ is F and $R^4$ is F, or $R^3$ is OH and $R^4$ is H;
$R^5$ is H and $R^6$ is OH, or $R^5$ is H and $R^6$ is H, or $R^5$ is H and $R^6$ is F, or $R^5$ is F and $R^6$ is H, or $R^5$ is F and $R^6$ is F, or $R^5$ is OH and $R^6$ is H;
$R^7$ is selected from the group consisting of: $CH_3$, $CH_2F$, $CHF_2$, and $CH_2OH$; and
$R^8$ is selected from the group consisting of: $C_{2-10}$ alkenyl, $C_{2-10}$ alkynyl, $C_{8-20}$ arylalkyl, $C_{8-20}$ arylalkenyl, $C_{8-20}$ arylalkynyl, each excluding H optionally substituted from one to four substituents with one of more of halo, OH, $OCF_3$, CN, $SO_2NH_2$, $SO_2Me$, $C(O)NH_2$, $CH_2F$, $CHF_2$, $CF_3$, $CH_2CH_2F$, $CH_2CF_3$, $CH_2CH_2CH_2F$, $C_{1-6}$ alkyl, $C_{1-6}$ alkoxy, or $C_{3-7}$ cycloalkyl.

2. The compound of claim 1 wherein the compound is selected from the following group:
N-((3S,4R,5R,6R)-4,5-dihydroxy-6-(hydroxymethyl)-1-(4-phenylbutyl)piperidin-3-yl)acetamide;
N-((3S,4R,5R,6R)-4,5-dihydroxy-6-(hydroxymethyl)-1-phenethylpiperidin-3-yl)propionamide;
N-((3S,4R,5R,6S)-6-(fluoromethyl)-4,5-dihydroxy-1-phenethylpiperidin-3-yl)propionamide;
N-((3S,4R,5R,6R)-4-fluoro-5-hydroxy-6-(hydroxymethyl)-1-phenethylpiperidin-3-yl)propionamide;
N-((3S,4R,5R,6S)-6-(difluoromethyl)-4,5-dihydroxy-1-phenethylpiperidin-3-yl)propionamide;
N-((3S,4R,5R,6R)-4,5-dihydroxy-6-(hydroxymethyl)-1-(3-phenylpropyl)piperidin-3-yl)propionamide;
N-((3S,4R,5R,6R)-4-fluoro-5-hydroxy-6-(hydroxymethyl)-1-(3-phenylpropyl)piperidin-3-yl)propionamide;
N-((3S,4R,5R,6R)-5-fluoro-4-hydroxy-6-(hydroxymethyl)-1-(3-phenylpropyl)piperidin-3-yl)propionamide;
N-((3S,4R,5R,6S)-6-(fluoromethyl)-4,5-dihydroxy-1-(3-phenylpropyl)piperidin-3-yl)propionamide;
N-((3S,4S,5R,6R)-4-fluoro-5-hydroxy-6-(hydroxymethyl)-1-(3-phenylpropyl)piperidin-3-yl)propionamide;
N-((3S,4R,5S,6R)-5-fluoro-4-hydroxy-6-(hydroxymethyl)-1-(3-phenylpropyl)piperidin-3-yl)propionamide;
N-((3S,4R,5R,6S)-6-(difluoromethyl)-4,5-dihydroxy-1-(3-phenylpropyl)piperidin-3-yl)propionamide;
N-((3S,4R,5R,6S)-6-(difluoromethyl)-4-fluoro-5-hydroxy-1-(3-phenylpropyl)piperidin-3-yl)propionamide;
N-((3S,4S,5R,6S)-6-(difluoromethyl)-4-fluoro-5-hydroxy-1-(3-phenylpropyl)piperidin-3-yl)propionamide;
N-((3R,5S,6R)-5-hydroxy-6-(hydroxymethyl)-1-(3-phenylpropyl)piperidin-3-yl)propionamide;
N-((3S,4S,6S)-4-hydroxy-6-(hydroxymethyl)-1-(3-phenylpropyl)piperidin-3-yl)propionamide;
N-((3S,4R,5R,6R)-4,5-dihydroxy-6-methyl-1-(3-phenylpropyl)piperidin-3-yl)propionamide;
N-((3S,4R,5R)-4,5-dihydroxy-1-(3-phenylpropyl)piperidin-3-yl)propionamide;
N-((3S,4R,5R)-4-fluoro-5-hydroxy-1-(3-phenylpropyl)piperidin-3-yl)propionamide;
N-((3S,4R,5R,6R)-1-(3-(6-fluoropyridin-3-yl)propyl)-4,5-dihydroxy-6-(hydroxymethyl)piperidin-3-yl)propionamide;
N-((3S,4R,5R,6R)-4,5-dihydroxy-6-(hydroxymethyl)-1-(3-(5-(trifluoromethoxy)benzo[d]thiazol-2-yl)propyl)piperidin-3-yl)propionamide;
N-((3S,4R,5R,6R)-4,5-dihydroxy-6-(hydroxymethyl)-1-((Z)-5,5,5-trifluoropent-3-en-1-yl)piperidin-3-yl)propionamide;
N-((3S,4R,5R,6R)-4,5-dihydroxy-6-(hydroxymethyl)-1-(pent-4-yn-1-yl)piperidin-3-yl)propionamide;
N-((3S,4R,5R,6R)-1-cinnamyl-4,5-dihydroxy-6-(hydroxymethyl)piperidin-3-yl)propionamide;
N-((3S,4R,5R,6R)-4,5-dihydroxy-6-(hydroxymethyl)-1-(3-phenylprop-2-yn-1-yl)piperidin-3-yl)propionamide;
N-((3S,4R,5R,6R)-1-((E)-3-(6-fluoropyridin-3-yl)allyl)-4,5-dihydroxy-6-(hydroxymethyl)piperidin-3-yl)propionamide;
N-((3S,4R,5R,6R)-1-(3-(6-fluoropyridin-3-yl)prop-2-yn-1-yl)-4,5-dihydroxy-6-(hydroxymethyl)piperidin-3-yl)propionamide;

or a pharmaceutically acceptable salt of any of the foregoing compounds.

3. The compound of claim 1 wherein the compound selectively inhibits an O-glycoprotein 2-acetamido-2-deoxy-β-D-glucopyranosidase (O-GlcNAcase).

4. The compound of claim 1 wherein the compound selectively binds an O-GlcNAcase.

5. The compound of claim 1 wherein the compound selectively inhibits the cleavage of 2-acetamido-2-deoxy-β-D-glucopyranoside (O-GlcNAc).

6. The compound of claim 4 wherein the O-GlcNAcase is a mammalian O-GlcNAcase.

7. The compound of claim 1 wherein the compound does not substantially inhibit a mammalian β-hexosaminidase.

8. A pharmaceutical composition comprising the compound of claim 1 or a pharmaceutically acceptable salt thereof in combination with a pharmaceutically acceptable carrier.

9. A compound selected from the following group:
N-((3S,4R,5R)-1-hexyl-4,5-dihydroxypiperidin-3-yl)acetamide;
N-((3S,4R,5R,6R)-4,5-dihydroxy-6-(hydroxymethyl)-1-(3-phenylpropanoyl)piperidin-3-yl)propionamide;
N-((3S,4R,5R,6R)-4,5-dihydroxy-6-(hydroxymethyl)-1-(4,4,4-trifluorobutyl)piperidin-3-yl)propionamide;
N-((3S,4R,5R,6R)-1-butyryl-4,5-dihydroxy-6-(hydroxymethyl)piperidin-3-yl)propionamide;
N-((3S,4R,5R,6R)-1-(3-(6-fluoropyridin-3-yl)propanoyl)-4,5-dihydroxy-6-(hydroxymethyl)piperidin-3-yl)propionamide;
or a pharmaceutically acceptable salt of any of the foregoing compounds.

* * * * *